(12) United States Patent
Lathe et al.

(10) Patent No.: US 6,420,353 B1
(45) Date of Patent: Jul. 16, 2002

(54) USE OF 7 α-SUBSTITUTED STEROID TO TREAT NEUROPSYCHIATRIC, IMMUNE OR ENDOCRINE DISORDERS

(75) Inventors: Richard Lathe; Kenneth Andrew Rose; Jonathan Robert Seckl; Ruth Best; Joyce Lai Wah Yau; Caroline McKenzie Leckie, all of Edinburgh (GB)

(73) Assignee: BTG International Limited, London (GB)

( * ) Notice: Subject to any disclaimer, the term of this patent is extended or adjusted under 35 U.S.C. 154(b) by 0 days.

(21) Appl. No.: 09/168,218

(22) Filed: Oct. 8, 1998

Related U.S. Application Data

(63) Continuation of application No. PCT/GB97/00955, filed on Apr. 4, 1997.

(30) Foreign Application Priority Data

| Apr. 9, 1996 | (GB) | 9607289 |
| Apr. 24, 1996 | (GB) | 9608445 |
| Mar. 10, 1997 | (GB) | 9704905 |

(51) Int. Cl.⁷ ............................................... A61K 31/56
(52) U.S. Cl. .................................................... 514/182
(58) Field of Search ........................................ 514/182

(56) References Cited

U.S. PATENT DOCUMENTS

| 2,418,603 A | 4/1947 | Schwenk et al. |
| 3,409,643 A | 11/1968 | Shapiro |
| 4,011,314 A | 3/1977 | Petzoldt et al. |
| 5,763,433 A | 6/1998 | Morfin |

FOREIGN PATENT DOCUMENTS

| BE | 834489 | 4/1976 |
| EP | 0 648 842 A2 | 4/1995 |
| GB | 1111860 | 3/1967 |
| GB | 1478356 | 6/1974 |
| GB | 1528796 | 10/1975 |
| GB | 1554965 | 12/1975 |
| WO | WO 92/03925 | 3/1992 |
| WO | 94/03176 | 2/1994 |
| WO | WO 95/06472 | 3/1995 |
| WO | 96/12810 | 5/1996 |
| WO | WO 96/35428 | 11/1996 |

OTHER PUBLICATIONS

Sapolsky et al, "the Neuroendocrinology of Stress and Aging. The . . . ," Endocrine Reviews, vol. 7, No. 3, pp. 284–285 (1986).
Rose et al, "Cyp7b, a novel brain cytochrome P450, . . . ," Proc. Natl. Acad. Sci. USA, vol. 94, pp. 4925–4930 (1997).
Avey et al, Journal of Endocrinology, vol. 152 (supplement) (1997).
Stapleton et al, "A Novel Cytochrome P450 Expressed Primarily in Brian," vol. 270, No. 50, Issue of Dec. 15, pp. 29739–29745 (1995).
J. Steroid Biochem. (1985), 23(2), 239–241 CODEN: JSTBBK; ISSN: 0022–4731.
J. Chem. Soc., Perkin Trans. 1 (1973), (14) 1462–1464 CODEN: JCPRB4.
Steroids (1979), 34(4), 381–400 CODEN: STEDAM; ISSN: 0039–128X.
Eur. J. Biochem. (1978), 84(1), 257–66 CODEN: EJBCAI; ISSN; 0014–2956.
C. R. Hebd. Seances Acad. Sci., Ser. C (1976), 283(11), 507–10 CODEN: CHDCAQ.
Endocrinology (Philadelphia) (1977), 100(2), 513–19 CODEN: ENDOAO.
J. Labelled Compd. Radiopharm. (1976), 12(2), 213–18 CODEN: JLCRD4.
J. Steroid Biochem. (1976), 7(2), 139–43 CODEN: JSTBBK.
Hoppe–Seyler's Z. Physiol. Chem. (1976), 357(1), 67–74 CODEN: HSZPAZ.
Biochem. J. (1975), 151(3), 513–18 CODEN: BIJOAK.
Hoppe–Seyler's Z. Physiol. Chem. (1974), 355(10), 1305–15 CODEN: HSZPAZ.
Chem. Pharm. Bull. (1974), 22(5), 1167–73 CODEN: CPBTAL.
Endokrinologie (1970), 57(1), 115–24 CODEN: ENDKAC.
J. Label. Compounds (1970), 6(4), 355–61 CODEN: JLCAAI.
Acta Endocrinol. (Copenhagen) (1969), 61(3), 416–76 CODEN: ACENA7.
Arch. Gynaekol. (1969), 207(4), 539–49 CODEN: ARGYAJ.
Abh. Dtsch. Akad. Wiss. Berlin, Kl. Med. (1966), vol. Date 1965, (3), 783–6 CODEN: ADWMAX.
Z. Physiol. Chem. (1967), 348(5), 581–4 CODEN: ZPCHA5.
Morfin et al (1994) Poster D103 at IX International Congress Hormonal Steroids, Dallas, Texas, USA.
Morfin and Courchay (1994) J. Steroid Biochem Molec. Biol. vol. 50, No. 1–2, p91–100.

(List continued on next page.)

Primary Examiner—T J Criares
(74) Attorney, Agent, or Firm—Nixon Vanderhye

(57) ABSTRACT

Use is provided for a 7α-hydroxy or 7-oxo substituted 3β-hydroxy-steroid possessing the carbon skeleton of cholesterol, androsterone, pregnenolone or estradiol, or an analogue thereof substituted independently at one or both of the 7- and 3-positions with an ester or ether group, in the manufacture of a pharmaceutical composition for the therapy of neuropsychiatric, immune and/or endocrine disorders or for inducing cognitive enhancement. Uses for Cyp7b enzymes in producing such steroids is also provided together with various novel steroids and test kits and methods for diagnosing the disorders.

5 Claims, 5 Drawing Sheets

OTHER PUBLICATIONS

Steroids (1999), 64(5), 363–370 CODEN: STEDAM; ISSN: 0039–128X.
Steroids (1998), 63(3), 141–145 CODEN: STEDAM; ISSN: 0039–128X.
J. Med. Chem. (1997), 40(22), 3659–3669 CODEN: JMCMAR; ISSN: 0022–2623.
Biol. Pharm. Bull. (1995), 18(8), 1120–5 CODEN: BPBLEO; ISSN: 0918–6158.
J. Med. Chem. (1989), 32(7), 1642–52 CODEN: JMCMAR; ISSN: 0022–2623.
Cancer Res. (1988), 48(19), 5460–5 CODEN: CNREA8; ISSN: 0008–5472.
Pharmacol. Toxicol. (Copenhagen) (1988), 63(4), 248–52 CODEN: PHTOEH.
J. Med. Chem. (1988), 31(3), 572–6 CODEN: JMCMAR; ISSN: 0022–2623.
J. Pharmacobio–Dyn. (1987), 10(7), 302–8 CODEN: JOPHDQ; ISSN: 0386–846X.
J. Steroid Biochem. (1984), 20(3), 785–7 CODEN: JSTBBK; ISSN: 0022–4731.
Prog. Cancer Res. Ther. (1983), 25(Steroids Endometrial Cancer), 77–84 CODEN: PCRTDK; ISSN: 0145–3726.
Recl.: J. R. Neth. Chem. Soc. (1983), 102(10), 433–7 CODEN: RJRSDK.
J. Chromatogr. (1983), 277, 71–7 CODEN: JOCRAM; ISSN: 0021–9673.
J. Chem. Soc., Perkin Trans. 1 (1982), (12), 2877–80 CODEN: JCPRB4; ISSN: 0300–922X.
Gen. Comp. Endocrinol. (1983), 49(3), 490–5 CODEN: GCENA5; ISSN: 0016–6480.
J. Chromatogr. (1982), 235(2), 523–6 CODEN: JOCRAM; ISSN: 0021–9673.

USE OF 7 α-SUBSTITUTED STEROID TO TREAT NEUROPSYCHIATRIC, IMMUNE OR ENDOCRINE DISORDERS

This is a continuation of PCT application No. PCT/GB97/00955, filed Apr. 4, 1997.

The present invention relates to novel uses for 7α-hydroxy-substituted steroids, to a process for preparing such steroids and to novel steroids so produced.

In particular the invention relates to the use of cytochromes of the cytochrome P450 family designated Cyp7b to effect 7α-hydroxylation of certain 3β-OH steroids so as to produce a 7α-hydroxy-substituted steroids. Certain of the 7α-hydroxy-substituted steroids so produced, as well the corresponding 7-oxo derivatives, are novel and form further aspects of the invention. The invention also relates to uses of these steroids, to uses of Cyp7b enzymes and to uses of novel macromolecular species, e.g. antibodies and DNAs, which are biologically related to the Cyp7b enzymes.

Cytochromes P450 are a diverse group of heme-containing mono-oxygenases (termed CYP's; see Nelson et al., DNA Cell Biol. (1993) 12, 1–51) that catalyse a variety of oxidative conversions, notably of steroids but also of fatty acids and xenobiotics. While CYP's are most abundantly expressed in the testis, ovary, placenta, adrenal and liver, it is becoming clear that the brain is a further site of CYP expression. Several CYP activities or mRNA's have been reported in the nervous system but these are predominantly of types metabolizing fatty acids and xenobiotics (subclasses CYP2C, 2D, 2E and 4). However, primary rat brain-derived glial cells have the capacity to synthesize pregnenolone and progesterone in vitro. Mellon and Deschepper, Brain Res. (1993), 629, 283–292(9) provided molecular evidence for the presence, in brain, of key steroidogenic enzymes CYP11A1 (scc) and CYP11B1 (11β) but failed to detect CYP17 (c17) or CYP11B2 (AS). Although CYP21A1 (c21) activity is reported to be present in brain, authentic CYP21A1 transcripts were not detected in this tissue.

Interest in steroid metabolism in brain has been fuelled by the finding that adrenal- and brain-derived steroids (neurosteroids) can modulate cognitive function and synaptic plasticity. For instance, pregnenolone and steroids derived from it are reported to have memory enhancing effects in mice. However, the full spectrum of steroid metabolizing CYP's in brain and the biological roles of their metabolites in vivo has not been established.

Many aspects of brain function are modulated by steroids. Intracellular receptors for glucocorticoids (cortisol, corticosterone) are particularly abundantly expressed in the hippocampus (1), a brain region that plays a key role in specific aspects of memory formation, and which is an early and prominent target for dysfunction and damage in Alzheimer's disease (AD). While glucocorticoids regulate learning and memory, mood and neuroendocrine control, chronic glucocorticoid excess compromises neuronal activity, synaptic plasticity and eventually survival, particularly in the hippocampus. These findings prompted the suggestion that glucocorticoid-mediated neurotoxicity might underpin some age-related brain disorders, including AD, in which plasma cortisol levels are markedly elevated (2).

Conversely, dehydroepiandrosterone (DHEA), the most abundant steroid product of the human adrenal cortex, has been proposed to protect against disorders of the aging brain (3). Plasma levels of DHEA often show a striking age-associated decline which correlates with loss of cognitive function (4). In rodents, injection of DHEA or its sulfate into limbic structures improves post-training memory and enhances synaptic plasticity (5). DHEA and glucocorticoids thereby appear to exert inverse effects upon memory function and synaptic plasticity, and DHEA has been advocated as an endogenous 'anti-glucocorticoid'. However, despite considerable circumstantial evidence to support this contention, there is no evidence for a direct interaction between DHEA and glucocorticoid signalling pathways in neurons.

Neurosteroidogenesis has been reported in isolated rat retina (8) and brain (9). In addition to the production of pregnenolone and DHEA from cholesterol, a variety of novel steroids are made in brain extracts or cultured brain cells, including 20α-dehydropregnenolone, 7α-hydroxy derivatives of pregnenolone and DHEA, progesterone, and both 3α- and 3β-hydroxy-5α-pregnan-20-one (reviewed in Ref. 7). Androgens are also modified, particularly through the action of aromatase and a 5α-reductase (reviewed in Ref. 10). However, the specific enzymes responsible for these and other transformations in the central nervous system have not been well characterized.

As referred to above, several Cyps are present in the central nervous system (11–22). Activities or mRNAs corresponding to key steroidogenic enzymes (23–25), in addition to Cyp19 (aromatase) have been detected. Furthermore, mRNAs encoding the non-Cyp hydroxysteroid dehydrogenases (HSD) 3α-HSD, 3β-HSD and 11β-HSD have been reported in the central nervous system (25, 27–29).

To investigate regulation of brain function, studies reported in copending International Patent Application No PCT/GB95/02465, published as WO 96/12810, and in Stapleton et al (J. Biol. Chem. 270, 29739–1995, Dec. 15, 1995), focused on the hippocampus, a brain region important in learning and memory. A copy of the specification of International Patent Application No PCT/GB95/02465 has been filed with the priority documents filed in respect of this specification.

That copending application, PCT/GB95/02465, describes and claims novel cytochrome P450 proteins designated Hct-1. These Hct-1 proteins have now been named as Cyp7b by the Committee on Standardized Cytochrome P450 Nomenclature and the name Cyp7b will be used in this application.

The Cyp7b enzyme shares 39% sequence identity to hepatic cholesterol 7α-hydroxylase (Cyp7a) and lesser but significant homology with other steroidogenic Cyps. The postulated steroidogenic domain (30,31), found in many of these enzymes, is present in both Cyp7a and Cyp7b. Cyp7b mRNA is predominantly expressed in rodent brain, particularly in the hippocampus, unlike Cyp7a, which is liver-specific (31–33 and EP0648840 A2).

The present inventors have now investigated the substrate specificity of Cyp7b and found that Cyp7b catalyses the introduction of a hydroxyl group at the 7α position in steroid substrates, particularly 3β-hydroxy steroids. Cytochromes Cyp7b are thus steroid hydroxylase enzymes having 7α-specificity. The ability to produce 7α-hydroxylated steroids is of major commercial importance, because such steroids are of particular use in the manufacture of pharmaceuticals (either as drugs per se or as intermediates), and in the manufacture of test kits and assays for pathological conditions associated with the presence of abnormal levels of endogenous enzyme, substrate or product.

The abbreviation "DHEA" will be used herein to designate dehydroepiandrosterone, thus 7α-hydroxy-DHEA designates 7α-hydroxydehydroepi-androsterone.

The present inventors have identified substrate/product pairs associated with Cyp7b, particularly DHEA/7α- hydroxy-DHEA (7-HD), pregnenolone/7α-hydroxy-pregnenolone (7-HP) and β-estradiol/7α-hydroxy-β-estradiol (7-HE). They have also determined that DHEA concentration in brain tissue declines with age, whereas the concentrations of other brain steroids do not, and determined that the ageing process may be associated with deficits in certain steroids and also with deficits in the concentration of Cyp7b itself. It is also believed that one of the products produced by Cyp7b mediated reactions, namely 7α-hydroxy dehydroepiandrosterone, plays an important role in the operation of the immune system. Because 7α-hydroxy-DHEA is believed to be made substantially only in the brain, the inventors hypothesize that senescence may be due to a deficit in brain-produced 7α-hydroxy-DHEA as well as in other steroids found in the brain such as DHEA, pregnenolone and 7α-hydroxy-pregnenolone.

The present inventors have now further determined that one of the specific properties of the 7α-hydroxy-substituted steroids, and potentially their 7-oxo substituted steroid derivatives, provided by the present invention is that of glucocorticoid and/or mineralocorticoid antagonism, whether at receptor level or otherwise. This is particularly demonstrated by the Example 5 below with respect to 7α-hydroxy-DHEA but is more generally applicable. Thus this activity not only gives further uses for the novel steroids of the invention but provides first and second medical uses for known 7α-hydroxy or 7-oxo steroids made available by the present process as glucocorticoid and/or mineralocorticoid antagonists and preferably in antagonism specific to neuronal tissue such as in the CNS.

Thus, having regard to this activity and their involvement in endogenous metabolic pathways, particularly in the brain, the 7α-hydroxy substituted 3β-hydroxy-steroids provided by use of the Cyp7b enzyme activity, including novel compounds provided by the invention, and their 7-oxo derivatives, have utility in the therapy of neuropsychiatric, immune and endocrine disorders, particularly but not exclusively steroid associated disorders.

Use of these 7α-hydroxy or 7-oxo substituted 3β-hydroxy-steroids, preferably possessing the carbon skeleton of cholesterol, androsterone, pregnenolone or estradiol, or derivatives thereof substituted independently at one or both of the 7- and 3-positions with an ester or ether group, in treating these disorders and for manufacturing medicaments for such treatment is provided in a first aspect of the present invention. Particularly preferred derivatives are those wherein one or both of the ester and or ether group is metabolisable in vivo to produce the corresponding hydroxy compound.

Preferred derivatives include those wherein the steroid has a 3β-substituent-$OR_1$ and/or a 7α-substituent —$OR_2$ where —$OR_1$ and —$OR_2$ each independently represents a free hydroxy, ester or ether group, wherein each of $R_1$ and $R_2$ are independently selected from the group consisting of hydrogen, substituted or unsubstituted $C_{1-6}$ alkyl groups, groups $R_5CO$—, wherein $R_5$ may be selected from substituted or unsubstituted $C_{1-6}$ alkyl groups, and groups of the formula —$OP(OH)_3$, wherein any substituents are selected from OH, halogen (F, Cl, Br, I) amino, $C_{1-6}$ alkylamino, $C_{1-6}$ dialkylamino, COOH or $COOR_4$ wherein $R_4$ represents a $C_{1-6}$ alkyl group; and wherein the compounds may be in free form or in the form of acid addition salts with pharmacologically acceptable anions.

The particular disorders for which this utility is provided include (a) deficits of cognition in aging
(b) Alzheimer's disease
(c) deficits of immune system in aging
(d) deficits of immune function in HIV infection
(e) glucocorticoid or mineralocorticoid excess
(f) diabetes
(g) depression
(h) osteoporosis and hypercalcemia
(I) hyperglycemia and hyperlipodemia
(j) muscle atropy
(k) arterosclerosis
(l) steroid diabetes Further, these 7α-hydroxy steroids, their esters, ethers and 7-oxo derivatives may be used to induce cognitive enhancement in a normal individual.

Preferred steroids for such use have the carbon skeleton of androsterone, pregnenolone or estradiol and particularly preferred examples are 7α-hydroxy-DHEA and 7α-hydroxypregnenolone. Accordingly the present invention further provides the use of novel compounds of Formula Ia and Ib shown below in the applications indicated above.

Particularly preferred uses for the antagonistic properties of these 7-substituted steroids include treatment of disorders falling within category (e) above or where reversal of the effects of such corticoids, regardless of excess, is required.

A second aspect of the present invention provides pharmaceutical compositions implementing such use. The compositions in which the novel steroids and known steroids of the invention will be used will readily occur to those skilled in the art, generally comprising the steroid active in association with a pharmaceutically acceptable carrier or diluent, with formulations for example being suitable for inhalation or for gastrointestinal (e.g. oral), parenteral, topical, transdermal or transmucosal administration.

As an alternative to administering the compounds of the invention per se, a third aspect of the invention provides the possibility of using the gene sequences of the Cyp7b genes in gene therapy in order to compensate for a deficiency in Cyp7b enzyme. In such therapies, constructs comprising Cyp7b coding sequences can be packaged in conventional delivery systems, such as andenoviruses, vaccinia viruses, herpes viruses and liposomes and administered via a route which results in preferential targeting of a selected tissue, especially the brain. The invention further provides the possibility of using the gene sequences of the Cyp7b genes in gene therapy in order to achieve the endogenous expression of Cyp7b sequences for other purposes, e.g. in order to promote immunogenic processes. Thus for example, a vector such as a suitably modified vaccinia virus (or variant thereof) may be co-administered with a vaccine formulation so that the expressed Cyp7b sequences augment the immunogenic properties of the vaccine.

It will be realised that in the event of Cyp7b related disorders other than those involving its depletion it may be desirable to use vectors containing antisense sequences to Cyp7b effective such as to inhibit Cyp7b expression.

Macromolecules related immunologically to Cyp7b enzymes form fourth and fifth aspects of the invention and in this regard antibodies, particularly monoclonal antibodies which are capable of selectively binding Cyp7b, have utility in the diagnosis of disorders (a) to (l) referred to above. Anti-Cyp7b antibodies (including monoclonal antibodies) as well as binding molecules comprising antibody fragments may be produced by known methods and used in test kits for assays for Cyp7b enzymes.

According to a sixth aspect of the invention, there is provided a process of producing a 7α-hydroxy-substituted steroid which comprises subjecting a corresponding steroid substrate having no hydroxyl substituent in the 7-position to hydroxylation in the presence of a Cyp7b steroid hydroxylase enzyme.

The Cyp7b steroid hydroxylase enzyme used in the process of the invention is preferably a Cyp7b enzyme described and claimed in the above-mentioned International Patent Application No PCT/GB95/02465 (and referred to therein as Hct-1). Such enzymes include (a) ones having the precise amino acid sequences described for mouse, rat and human Cyp7b, (b) homologous enzymes from other species and (c) enzymes having amino acid sequences which differ from the sequences of enzymes included in definitions (a) and (b), but in which the capacity to catalyse the introduction of a 7α-hydroxyl group is not eliminated.

The amino acid sequence of suitable Cyp7b steroid hydroxylase enzymes may be defined in terms of the DNA coding sequences disclosed in International Patent Application No PCT/GB95/02465. Thus the Cyp7b steroid hydroxylase enzyme may have a sequence encoded by DNA coding sequences of Cyp7b enzymes selected from (a) Coding sequences of DNA molecules comprising the coding sequence for rat Cyp7b set forth in SEQ Id No: 1, (b) Coding sequences of DNA molecules comprising the coding sequence for mouse Cyp7b set forth in SEQ Id No: 2, (c) Cyp7b steroid hydroxylase-encoding DNA molecules capable of hybridizing with the DNA molecule defined in (a) or (b) under standard hybridization conditions defined as 2×SSC at 65° C.

20 (d) Cyp7b steroid hydroxylase-encoding DNA molecules capable of hybridizing with the DNA molecule defined in (a), (b) or (c) under reduced stringency hybridization conditions defined as 6×SSC at 55° C.

The sequences (a) and (b) above represent rat and mouse Hct-1 gene sequence. Homologous sequences from other vertebrate species, especially mammalian species (including man) fall within the class of DNA molecules represented by (c) or (d).

Thus for human Cyp7b, the steroid hydroxylase enzyme may comprise a sequence encoded by (e) DNA coding sequences selected from the following:
(i) the sequence designated "exon 3" in SEQ Id No 3,
(ii) the sequence designated "exon 4" in SEQ Id No 3, and (f) Cyp7b steroid hydroxylase-encoding DNA molecules capable of hybridizing with the DNA molecules defined in (e) under standard hybridization conditions defined as 2×SSC at 65° C.

(g) Cyp7b steroid hydroxylase encoding DNA molecules capable of hybridizing with the DNA molecule defined in (e) or (f) under reduced stringency hybridization conditions defined as 6×SSC at 55° C.

(h) Cyp7b steroid hydroxylase-encoding DNA molecules comprising contiguous pairs of sequences selected from
(i) the sequence designated "exon 3" in SEQ Id No 3,
(ii) the sequence designated "exon 4" in SEQ Id No 3, and (i) Cyp7b steroid hydroxylase-encoding DNA molecules capable of hybridizing with the DNA molecules defined in (h) under standard hybridization conditions defined as 2×SSC at 65° C.

(j) Cyp7b steroid hydroxylase-encoding DNA molecules capable of hybridizing with the DNA molecule defined in (h) or (i) under reduced stringency hybridization conditions defined as 6×SSC at 55° C.

(k) Coding sequences of DNA molecules comprising a contiguous coding sequence consisting of the sequences "exon 3" and "exon 4" in SEQ Id No 3, and (l) Cyp7b steroid hydroxylase-encoding DNA molecules capable of hybridizing with the DNA molecules defined in (k) under standard hybridization conditions defined as 2×SSC at 65° C.

(m) Cyp7b steroid hydroxylase-encoding DNA molecules capable of hybridizing with the DNA molecule defined in (k) or (l) under reduced stringency hybridization conditions defined as 6×SSC at 55° C.

It will be appreciated that the DNA sequences referred to may consist of or be derived from genomic DNA, but typically would consist of or be derived from cDNA. Such sequences could be obtained by probing an appropriate library (cDNA or genomic) using hybridisation probes based upon the sequences provided according to the invention of International patent application No PCT/GB95/02465, or they could be prepared by chemical synthesis or by ligation of sub-sequences.

In the above definitions, Cyp7b steroid hydroxylases have been defined in terms of DNA sequence information. The Cyp7b steroid hydroxylase enzyme used in accordance with the process of the invention may alternatively or additionally be defined by reference to amino acid sequence information, e.g. the amino acid sequences contained in SEQ ID NO. 4, SEQ ID NO. 5 or SEQ ID NO 6.

Thus the Cyp7b steroid hydroxylase enzyme used in accordance with the process of the invention may have sequences matching one of said sequences exactly, or alternatively, the enzymes used may have sequences which differ from the aforementioned sequences, provided that the capacity to catalyse the introduction of a 7α-hydroxyl group is not eliminated.

Thus, for example, mutant enzymes may be produced by known methods, for example site-directed mutagenesis or other PCR-based procedures, and the expression products tested for their capacity to catalyse the introduction of a 7α-hydroxyl group in selected substrates in accordance with the procedures described herein.

Having regard to the degree of homology between the rat, mouse and human enzymes and known data relating to species divergence of hydroxylase enzymes, it is preferred that by comparison with the DNA sequences of SEQ ID NO. 1, SEQ ID NO. 2 and SEQ ID NO.3, the mutant enzymes should should be encoded by sequences having at least 50% homology, more preferably at least 60% homology and most prefereably at least 70% homology with said sequences over a length of 50 contiguous nucleotides.

Preferably the mutant enzymes are encoded by sequences having at least 60% homology with the entire coding sequence, more preferably at least 70%.

Alternatively, by comparison with the amino acid sequences of SEQ ID NO. 4, SEQ ID NO. 5 and SEQ ID NO.6, it is preferred that mutant enzymes should have at least 50% homology, more preferably at least 60% homology and most prefereably at least 70% homology with said sequences over a length of 30 contiguous amino acids. Preferably the mutant enzymes have at least 60% homology and more preferably 70% homology or more with the entire amino acid sequence in each case.

It is however preferred that such mutant enzymes do not differ too drastically from the aforementioned sequences and in this regard, where amino-acid substitutions are made, that the substituted amino acids are preferably so-called "synonymous" or "conservative" substitutions, i.e. hydrophilic, hydrophobic, basic and acidic amino acids should preferably be substituted by amino acids in the same class (see U.S. Pat. No. 5,380,712).

More specifically, it is preferred that the mutant enzymes differ from the precise sequences of those described herein by not more than 20, preferably not more than 10 and most preferably not more than 5 amino acid substitutions, insertions or deletions.

The Cyp7b enzymes described herein may be used in toxicological and drug evaluation studies and such uses form further aspects of the invention. In a particularly preferred embodiment of this aspect of the invention, a cell line capable of expressing a Cyp7b enzyme is used as a basis of an assay for one or more Cyp7b substrates. Such cell lines have utility in toxicological and drug evaluation studies. Most preferably the cell line comprises a prokaryotic or eucaryotic cell line which has been transformed so as artificially to express a Cyp7b enzyme. Examples include bacteria, yeast and mammalian cells. Also included are transgenic animals, at least one tissue of which (especially a non-brain tissue) expresses Cyp7b enzyme. Such transgenic animals may be produced by known methods for introducing foreign coding sequences into somatic or germ line cells.

The substrates used in the method of the invention are characterised by possessing a 3β-hydroxyl group and further by preferably possessing the carbon skeleton of cholesterol, androsterone, pregnenolone or estradiol, with the proviso that where the substrate has the carbon skeleton of cholesterol, the substrate has a hydroxyl group in the 25, 26 or 27-position, preferably the 25-position.

Examples of such substrates include 25-hydroxycholesterol, dehydroepiandrosterone, pregnenolone and estradiol, in which case the steroids produced will be 7α-hydroxy-25-hydroxycholesterol, 7α-hydroxydehydroepiandrosterone, 7α-hydroxy pregnenolone and 7α-hydroxyestradiol (i.e. estra 1,3,5(10)-triene-3,7α, 17β-triol) respectively.

The 7α-hydroxylated steroid produced according to the invention may be oxidised by known enzymatic or non-enzymatic procedures to produce 7-oxo substituted steroids and this further process step forms a further aspect of the invention.

Certain 7α-hydroxy-substituted steroids produced according to the invention and certain corresponding 7-oxo derivatives are novel and provide a further aspect of the invention. Thus the present invention further provides novel 3β-hydroxy steroids characterised in that they have a 7α-hydroxy or 7-oxo substitutuent. Preferred novel steroids have the carbon skeleton of cholesterol, androsterone, pregnenolone or estradiol, with the provisio that where the skeleton is that of cholesterol, the 25, 26 or 27 position is hydroxylated, most preferably the 25 position.

Particular novel steroids are of the formula

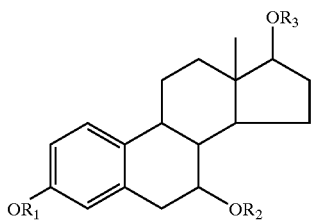

Ia

-continued

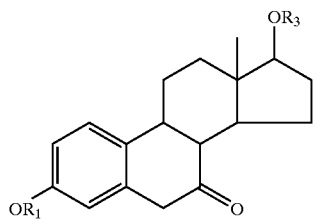

Ib wherein $OR_1$, $OR_2$ and $OR_3$ each independently represents a free hydroxy group, an ether group or an esterified hydroxy group.

In the case where $OR_1$, $OR_2$ and $OR_3$ each independently represents an ether group, each of $R_1$, $R_2$ and $R_3$ may be selected from substituted or unsubstituted $C_{1-6}$ alkyl groups, any such substituents being selected from OH, halogen (F, Cl, Br, I) amino, $C_{1-6}$ alkylamino, $C_{1-6}$ dialkylamino, COOH or $COOR_4$ wherein $R_4$ represents a $C_{1-6}$ alkyl group which may be unsubstituted or substituted by one of the substituents referred to above.

In the case where $OR_1$, $OR_2$ and $OR_3$ each independently represents an esterified hydroxy group, each of $R_1$, $R_2$ and $R_3$ may have the formula $R_5CO-$, wherein $R_5$ may be selected from substituted or unsubstituted $C_{1-60}$ alkyl groups, any such substituents being selected from OH, halogen (F, Cl, Br, I) amino, $C_{1-6}$ alkylamino, $C_{1-6}$ dialkylamino, COOH or $COOR_4$ wherein $R_4$ represents a $C_{1-6}$ alkyl group; and groups of the formula $-OP(OH)_3$. Where compounds of Formula Ia or Ib include substituents such as carboxyl groups, phospate groups, or substituted or unsubstituted amino groups, the compounds may be in free form or in the form of acid addition salts with pharmacologically acceptable anions (such as, for example, phosphate or halide ions) or cations (such as, for example, alkaline metal cations). Thus, where $OR_1$, $OR_2$ or $OR_3$ represents hemesuccinate $HOOC(CH_2)_2CO$, the resulting hemesuccinate may be in the form of, for example, an Na or K salt.

It will be realised that the present invention provides for 7α-hydroxylated and 7-oxo steroids as described above but which are further substituted at other positions directly on the steroid skeleton.

7α-Hydroxyestradiol and 7-oxoestradiol are specific examples of compounds of Formula Ia and Ib.

The invention will now be described in more detail with particular reference to the following Figures and Examples.

EXAMPLE 1

Figure 1:
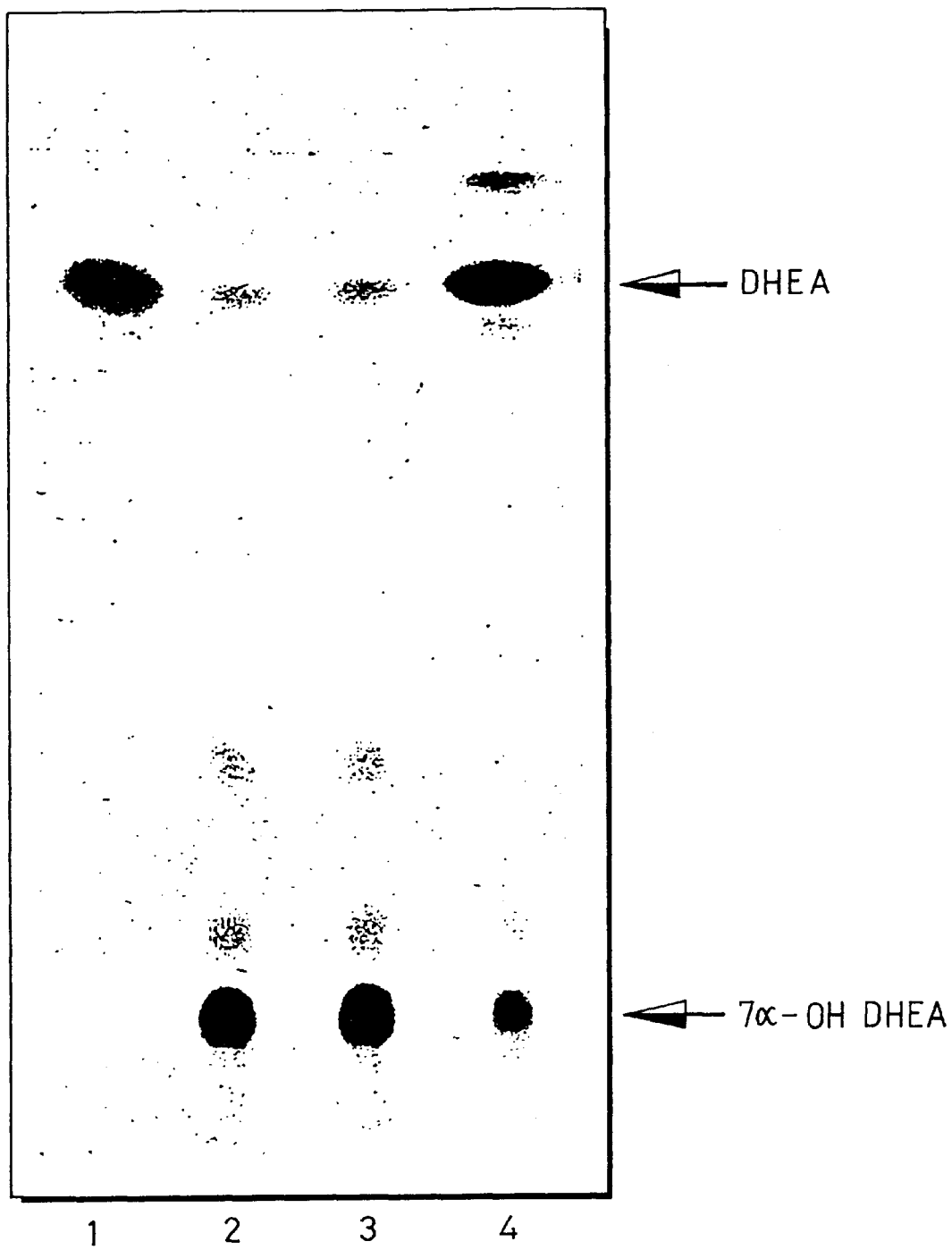
FIG. 1 illustrates an autoradiogram of a TLC plate used in an experiment to assess the ability of various cell extracts to hydroxylate DHEA.

Identification of Substrate Specificity of Mu Cyp7b

A. Preparation of Vaccinia Expression Construct

To identify the reaction catalysed by Cyp7b a cDNA encoding the mouse enzyme, reported by Lathe, Rose and Stapleton (PCT/GB95/02465) and by Stapleton et al. (J. Biol. Chem. 270, 29739—1995, Dec. 15, 1995), was modified to introduce a translation initiation consensus sequence at the 5' end of the Cyp7b open reading frame as described therein. The modified cDNA was introduced into the genome of vaccinia virus by recombinant exchange according to standard procedures (see, for instance, Gonzalez et al., Meth. Enzymol. 206, 85–92, 1991 and references therein) as described in Lathe et al.

B. Production of Cyp7b Enzyme Extracts

Hela cells were grown to semi confluence ($10^6$ cells per 5 cm dish; 5 ml medium) and infected with recombinant (VV-Cyp7b) and control (VV Copenhagen strain) vaccinia viruses at 0.1 pfu per cell; 16 hours later infected cells were washed and taken up into W (Waxman) buffer (0.1 M KP04, 1 mM EDTA, 20% glycerol pH 7.5; 500 µl per plate) and recentrifuged (5 min., 1000 rpm).

For whole cell extracts cells were resuspended into 1/100 volume (50 µl per plate) of W buffer and stored frozen at −70° C. For microsome preparation (Waxman, Biochem. J. 260, 81–85, 1989) cells were resuspended in 1/10 original volume of W buffer (500 µl per plate); sonicated 6×5 seconds on ice, and unbroken cells were removed by centrifugation (10 min., 4° C., 3000 rpm).

The microsomal fraction was prepared from the supernatant by centrifugation (100,000 g, 45 min., 4° C., Beckman SW50.1 rotor) and resuspended using a Potter homogeniser in 1/50 original volume of W buffer (100 µl per plate) before storage at −70° C.

Control extracts were prepared from liver and brain from male rat by homogenising fresh tissue in W buffer (2.5 ml/g), clarifying briefly by centrifugation (4000 rpm, 5 min, 4° C.); the supernatant was stored at −70° C.

C. Substrate Identification by Thin-layer Chromatography $^{14}$C or $^3$H-labelled steroids were purchased from DuPont-NEN ($^{14}$C-labelled molecules: specific activities 45–60 mCi/mmol.; $^3$H: specific activities 70–100 mCi/mmol). 1 nMol aliquots of labelled substrate were dried down, microsomes or cell and tissue extracts were added (25 to 50 µl), and diluted to a volume of 175 µl with W buffer.

Reaction was started by the addition of 25 µl of 8 mM NADPH. After incubation at 37° C. for 15 minutes the reaction was shaken with 500 µl of ethyl acetate (BDH). The organic phase was removed, dried down, and suspended into 10 µl ethyl acetate. Aliquots (5×2 µl) were applied to thin layer chromatography (TLC) sheets (Merck) and developed in ethyl acetate/n-hexane/acetic acid 16:8:1 (solvent system N of Waxman, Meth. Enzymol. 206, 462–476, 1991). After drying, chromatograms $^{14}$C were visualised by exposure to X-ray film. $^3$H-labelled chromatograms were treated with EN$^3$ HANCE™ (DuPont-NEN) spray prior to exposure.

D. Results

FIG. 1 is an autoradiogram of a TLC plate run in solvent system N; substrate was $^3$H-DHEA and samples were extracted with ethyl acetate and dried prior to application to the TLC plate (origin at bottom of figure). Extracts were 1, Microsomes from Hela cells infected with control vaccinia virus (negative control); 2, Microsomes from Hela cells infected with VVCyp7b; 3, Duplicate preparation of microsomes from Hela cells infected with VVCyp7b; 4, Rat brain homogenate.

As can be seen from FIG. 1, microsomes from cells infected with recombinant vaccinia expressing Cyp7b converted $^{14}$C-dehydroepiandrosterone (DHEA) to a lower mobility form most consistent with hydroxylation. Brain extracts yielded a product of indistinguishable mobility, consistent with our earlier demonstration that Cyp7b is expressed in brain. From the relative mobility of the product we surmised that Cyp7b could be hydroxylating DHEA at the 7 position. Progesterone, corticosterone, cortisol and testosterone were at best inefficiently metabolised, if at all. However, pregnenolone and estradiol were both converted by the enzymes, as was 25-hydroxy cholesterol. All these substrates are distinguished by a 3β hydroxy group.

EXAMPLE 2

Identification of the Position of the Modification by 3H-release

To Identify the position of the modification, $^3$H-pregnenolone (NEN) was employed in which the $^3$H substitution was predominantly at the 7 position on the steroid backbone. Microsomal extracts were incubated with $^3$H-pregnenolone under the same conditions as used earlier. Following reaction, labelled steroids were extracted with ethyl acetate (2×1 ml), and discarded; release of $^3$H into the aqueous phase was monitored by liquid scintillation counting.

Figure 2:
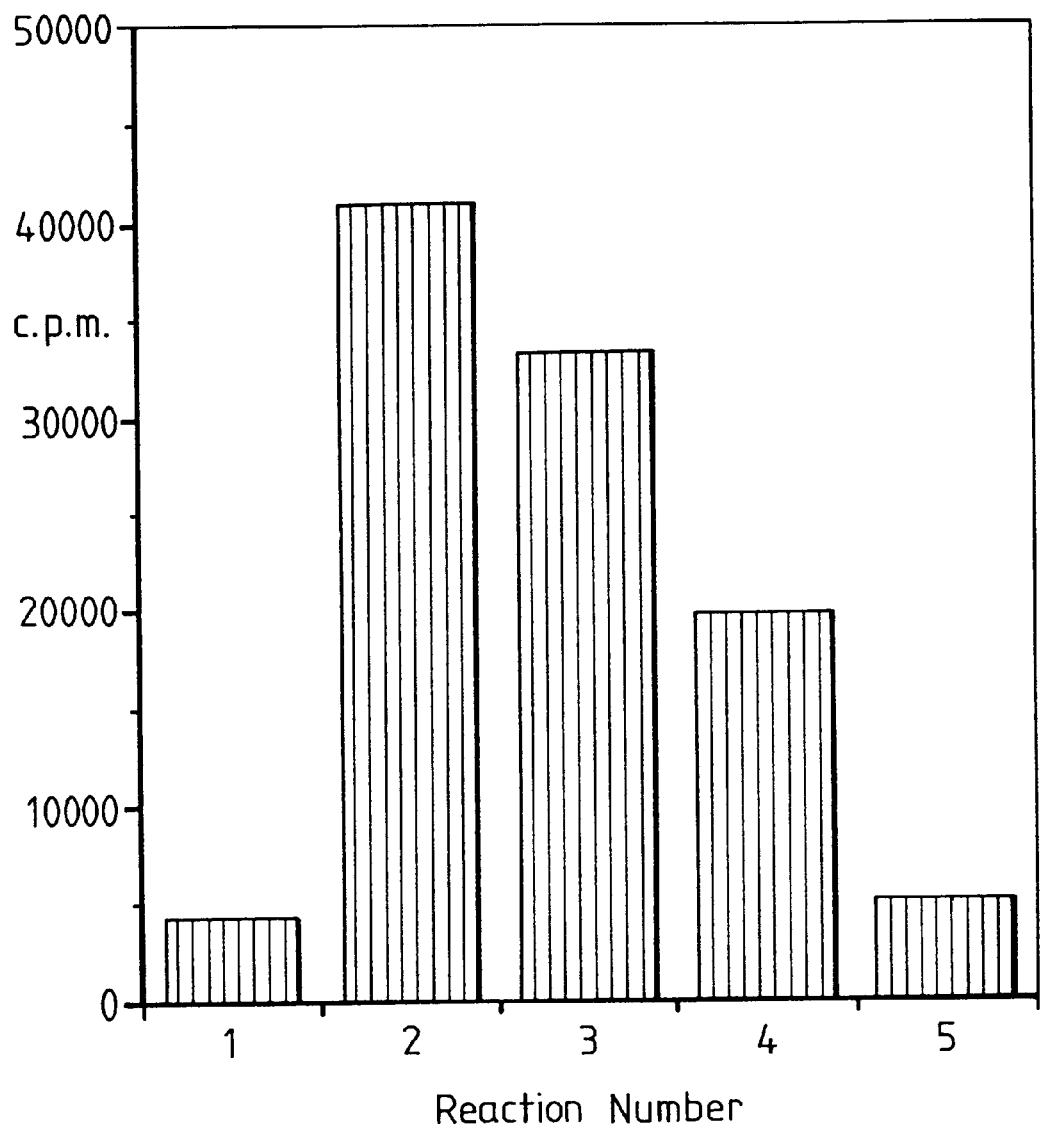
FIG. 2 depicts the ability of various tissues to release radioactivity from 7-$^3$H-pregnenolone.
Figure 3:
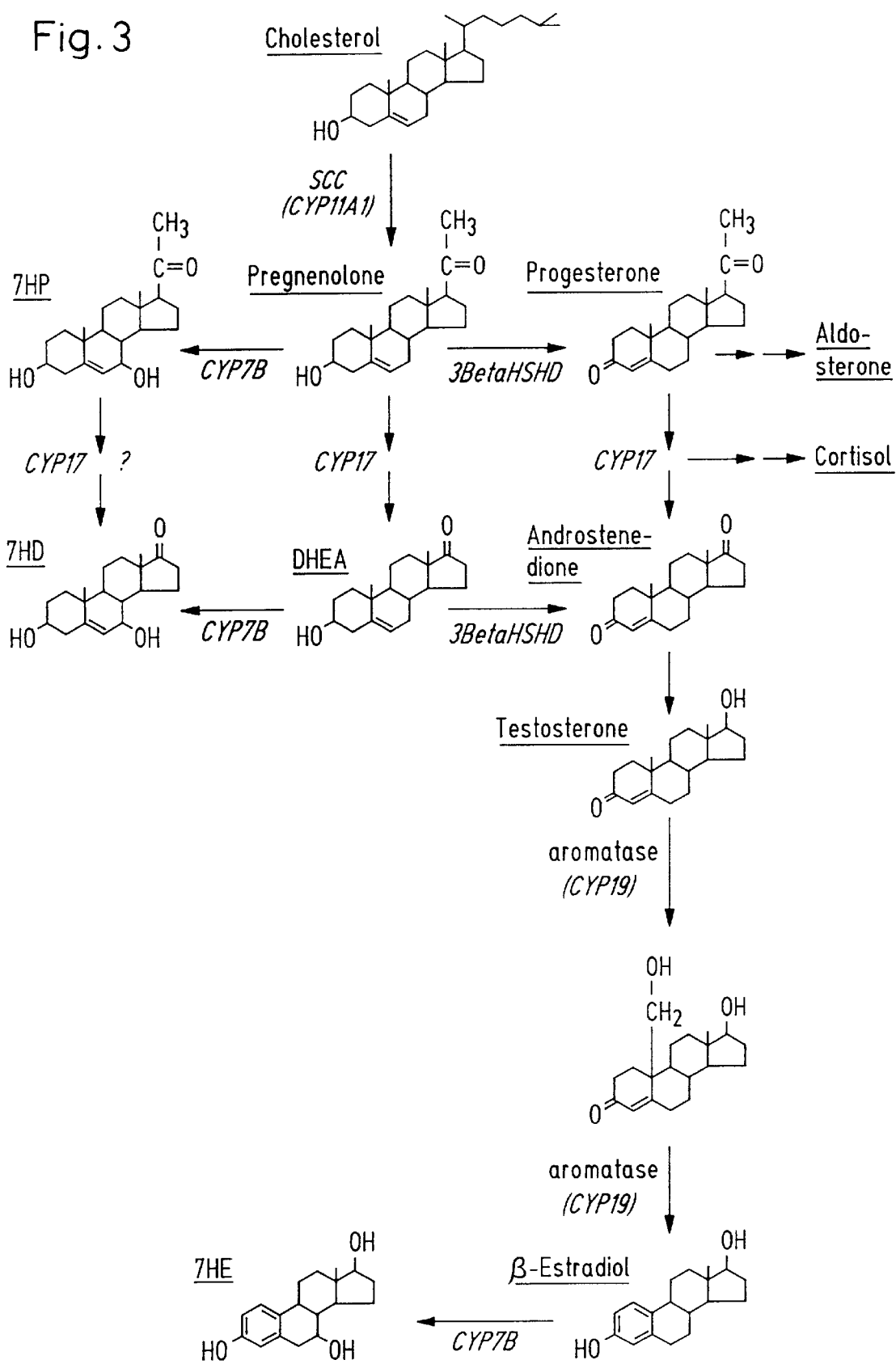
FIG. 3 illustrates the principal steroid interconversions mediated by Cyp7b.

Referring to FIG. 2, 7-$^3$H-pregnenolone was incubated with extracts and assayed for release of radioactivity into the aqueous phase following extraction with ethyl acetate. Extracts were 1, Microsomes from Hela cells infected with control vaccinia virus (negative control); 2, Microsomes from Hela cells infected with VVCyp7b; 3, Duplicate preparation of microsomes from Hela cells infected with VVCyp7b; 4, Rat brain homogenate; 5, Rat liver homogenate.

As seen in FIG. 2 microsomes from cells infected with recombinant vaccinia expressing Cyp7b efficiently released $^3$H into the aqueous phase. Brain also performed this reaction but not liver. Release of $^3$H from the 7 position of pregnenolone demonstrates that Cyp7b hydroxylates pregnenolone at the 7-position to generate 7-hydroxy pregnenolone (7HP); it may be concluded that Cyp7b also hydroxylates DHEA (to generate 7-hydroxy DHEA [7HD]) and estradiol to generate 7-hydroxy estradiol [7HE].

EXAMPLE 3

Stereochemistry of the Cyp7b Hydroxylation

Steroids hydroxylated at a variety of positions (egs. 2, 6, 7, 15, 16) differ in their mobility on TLC depending on whether the modification is in the α- or the β-position (Waxman, Meth. Enzymol. 206, 462–476, 1991). Purified 7α-hydroxy DHEA was obtained (kind gift of Dr. H. A. Lardy, Enzyme Institute, University of Wisconsin), mixed with the product of Cyp7b action on DHEA, and subjected to TLC. The product comigrated with 7α-hydroxy-DHEA, demonstrating that Cyp7b is a 7α hydroxylase.

EXAMPLE 4

Activity of Enzyme in 7α-hydroxylation of pregnenolone and DHEA

To examine the catalytic activity of the enzyme Cyp7b CDNAs were expressed in mammalian cell lines. Cell extracts showed substantial NADPH-dependent conversion of DHEA (Km 13.3 µM; Vmax 288 pmol/min/mg) and pregnenolone (Km 3.6 µM; Vmax 34 pmol/min/mg) to slower migrating forms on thin layer chromatography. Products of identical mobility were generated by rat brain extracts. The expressed enzyme was less active against 25-hydroxycholesterol, 17β-estradiol and 5α-androstane-3β, 17β-diol, with low to undetectable activity against progesterone, corticosterone and testosterone. When [$^3$H-7α] pregnenolone was incubated with Cyp7b extracts the extent of release of radioactivity into the medium suggested that hydroxylation was preferentially at the 7α-position. In gas chromatography and mass spectrometry of the modified steroid arising from incubation of DHEA with Cyp7b extracts, the retention time and fragmentation patterns were identical to those obtained with authentic 7α-hydroxy DHEA (7HD); the reaction product also co-migrating with 7HD on TLC.

Mass spectrometry: A 10× scaled up reaction was employed using 95% unlabelled DHEA (Sigma) and 5% [14C]-DHEA (final specific activity 2.25–3 mCi/mmol) and reaction time was extended to 1 hour. Product was purified by TLC, excised and extracted with ethyl acetate before drying down. The dried residue and authentic 7HD (50 mg) were converted to their methoxime-trimethylsilyl (MO-TMS) derivatives. Analysis of these products was performed using a Trio 100 mass spectrometer operating in electron impact (EI) mode, linked to a HP5890 gas chromatograph fitted with a HP-1 cross-linked methyl siloxane column (25 m, i.d. 0.25 mm, 0.17 mm film) under the following conditions: electron energy 70 eV, source temperature 200° C., interface temperature 280° C., oven temperature 50° C. increasing at 30° C. per minute to 200° C., and then 10° C. per minute to 300° C., injection temperture 280° C.

EXAMPLE 5
Cis-trans Co-transfection Assay; Demonstration of Antagonism

Chinese hamster ovary (CHO) cells were maintained and transfected in Dulbecco's modification of Eagle's medium (DMEM) supplemented with 15% foetal bovine serum, 100 IU/ml penicillin, 100 μg/ml streptomycin and 200 mM L-glutamine (all Gibco BRL, Paisley, UK).

24 hours prior to transfection CHO cells were plated at a density of 3×10$^5$/60 mm dish (Costar UK). Cells were transfected by the clacium phosphate method. Briefly, 5 μg of MMTV-LUC and 1 μg of pRShGR or 5 μg of pSV2 as a control for transfection efficiency were made up to a total of 10 μg/plate of DNA with pGEM3. 30 μl of 2.5M CaCl$_2$ was diluted ten-fold with sterile water and 300 μl was added to the DNA. Next 300 μl of 2× Hepes buffered saline (280 mM NaCl, 10 mM Kcl, 1.5 mM Na$_2$HPO$_4$.2H$_2$), 50 mM Hepes, 12 mM dextrose, pH 7.05) was added slowly with swirling to the DNA/CaCl$_2$ mixture. This solution was left for 30 minutes in order for a fine precipitate to form and 600 μl was added dropwise to each plate. After 24 hours the medium was removed and the cells were washed in serum free medium and culture for a further 24 hours in medium containing 10% charcoal-stripped serum together with the appropriate concentrations of DHEA/7α-hydroxy-DHEA.

Six hours after the addition of DHEA/7α-hydroxyDHEA either B or Dex was added to each plate. The following day the cells were washed in PBS, lysed with 0.3 ml of lysis buffer (25 mM Tris-phosphate pH 7.8, 2 mM DTT, 1% Triton X-100 and 10% glycerol), scraped, centrifuged and the supernatant assayed in duplicate in a Berthold luminometer in a total volume of 250 μl, comprising 40 μl of cell extract, 5 μl of 30 mM ATP, 100 μl of assay buffer (20 mM tricine, 1.07 nM (MgCO$_3$)$_4$.Mg(OH)$_2$.%H$_2$O, 2.67 mM MgSO$_4$, Q1 mM EDTA, 33.3 mM DTT, 0.2 mg/ml coenzyme A) and 105 μl luciferin (Promega UK) injected to initiate the reaction. Light emission was measured over 10 seconds and relative light units/microgram of protein was calculated.

Figure 4:
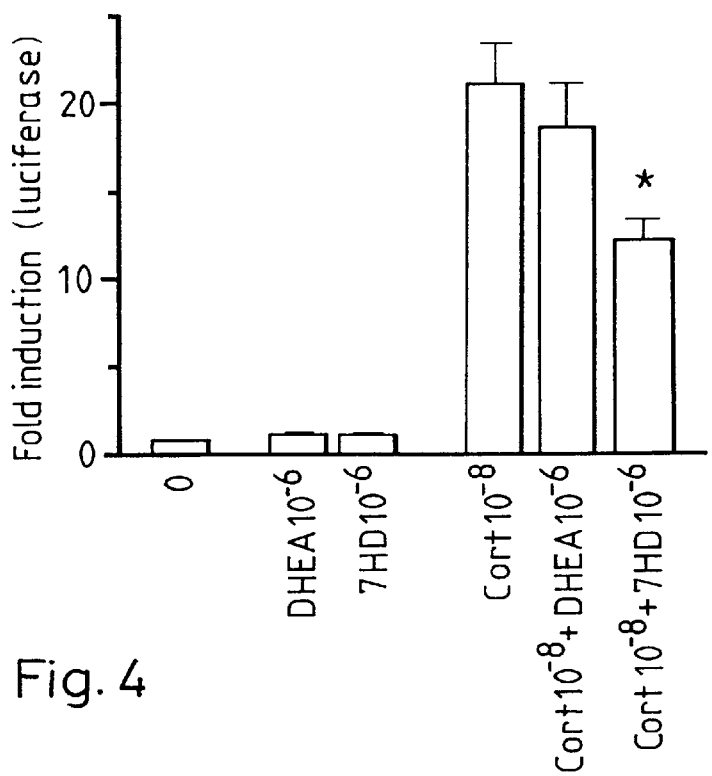
FIG. 4 is a histogram plotting fold induction of luciferase expression with concentration of various steroids as described in Example 5.

Results are shown in FIG. 4 wherein the fold induction of luciferase is illustrated by histogram for control, additions of DHEA, 7α-hydroxy-DHEA (7HD) alone and these additions in presence of an GR activating concentration of corticosterone. This result shows that 7HD, but not DHEA, acts as an antagonist of coticosterone effect in activating the GR-mediated transcription.

EXAMPLE 6
Cyp7b Expression in Alzheimers Neurons

Cryostat brain sections (10 μm) from control and Alzheimer's hippocarnpus were cut, thaw mounted onto gelatine-subbed poly-L-lysine coated slides and stored at −80° C.

For in-situ hybridization studies, brain sections were post-fixed in 4% paraformaldehyde by acetylation (0.25% acetic anhydride in 0.1M triethanolamine, pH 8.0) for 10 minutes, rinsed in phosphate buffered saline, dehydrated through graded alcohols and air dried. Hybridization was carried out using 200 μl of [$^{35}$S]-UTP-labelled cRNA antisense probe (10×10$^6$ dpm/ml in hybridization buffer) synthesized in vitro from a 500 bp Xbal/PstI fragment of the human Cyp7b pMMCtI clone linearised with XbaI and transcribed with T3 RNA for sense probes. Sections were prehybridized with 20 μl of prehybridization buffer (as hybridization buffer but omitting the dextran sulphate) per slide at 50° C. for 3 hours.

Following hybridization with probe at 50° C. overnight sections were treated with RNase A (30 μg/ml, 45 minutes at 37° C.) and washed to a final stringency of 0.1×SSC at 60° C. Slides were dehydrated, dipped in photographic emulsion (NTB-2, Kodak) and exposed at 4° C. for 5 weeks before being developed and counterstained with 1% pyronin. The density of silver grains was assessed over individual hippocampal neurons by computer-assisted grain counting using an image analysis system (Seescan plc, Cambridge, UK), with the analysis carried out blind (sections were cut and coded by a separate individual). For each slide, one hippocampal section represents each subject. 6–10 neurons/subregion were assessed and background, counted over areas of white matter, was subtracted. Data were assessed by ANOVA followed by Scheffe post hoc test. Significance was set at p<0.05. Values are means±S.E.M.

Figure 5:
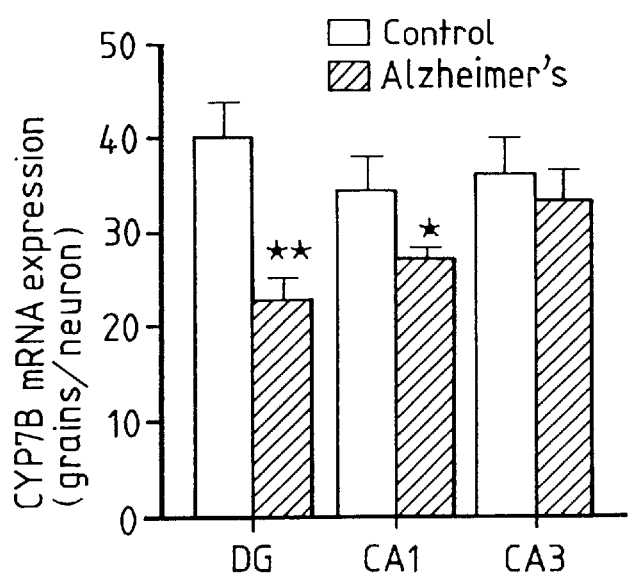
FIG. 5 illustrates the attenuation of Cyp7b gene expression in Alzheimer's as described in Example 5.
Figure 6A:
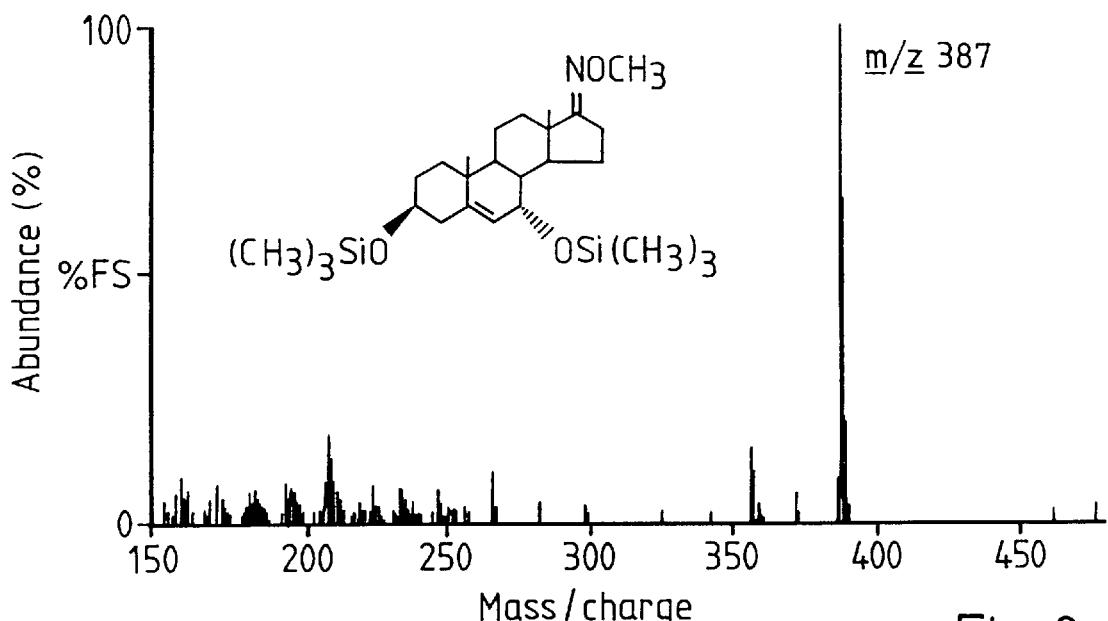
FIG. 6 shows mass spectrometer plots of 7α-hydroxy-DHEA produced by the present process and a reference sample thereof.
Figure 6B:
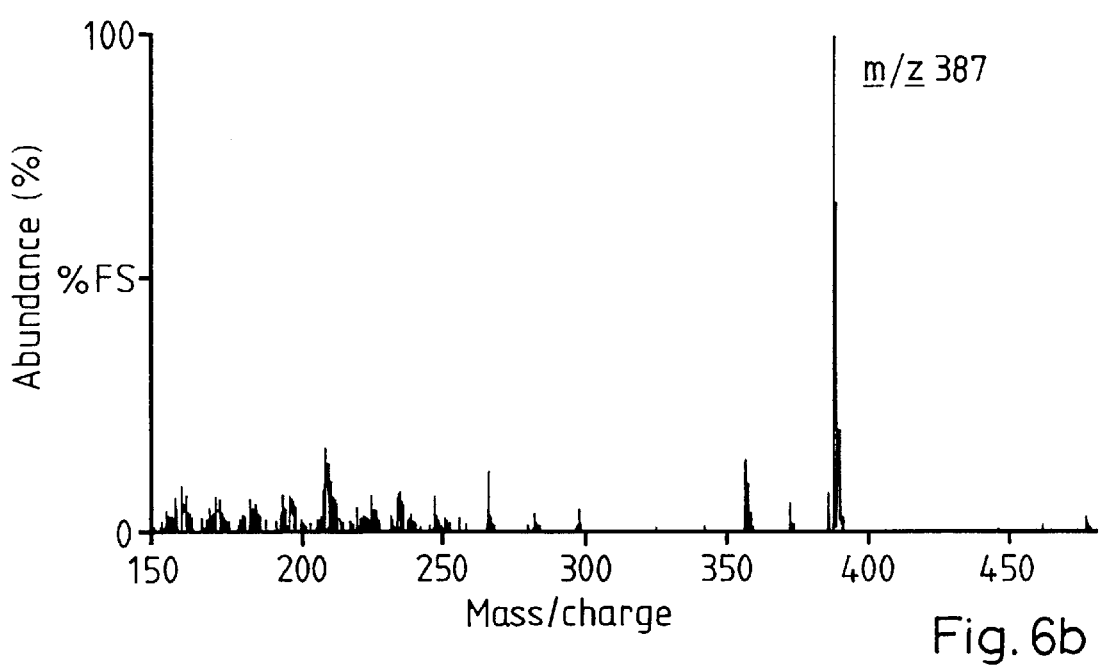

FIG. 5 is a histogram showing Cyp7b expression as indicated by grain count per neuron in the dentate gyrus, CA1 and CA3 subfields of Alzheimer's disease samples as compared to the age matched control brains.

CONCLUSIONS

It can be concluded that Cyp7b, and cognate enzymes from rat, human and other mammalian species, are 7α-hydroxylases specific for steroid substrates with a 3β hydroxy group. While activities for 7-hydroxylating DHEA, pregnenolone and cholesterol have been recorded previously in a variety of crude tissue homogenates (e.g. Akwa et al., Biochem. J. 288, 959–964, 1992) no characterisation of the enzyme responsible was performed previously and no activity on estradiol was recorded. Recombinant organisms expressing Cyp7b thus provide a route to the large scale manufacture of 7HP, 7HD, and 7HE, principally but not exclusively for therapeutic use or for the production of further steroid derivatives such as 7-oxo molecules.

REFERENCES

1. Joels, M. and de Kloet, E. R. (1994). Mineralocorticoid and glucocorticoid receptors in the brain. Implications for ion permeability and transmitter systems. Prog. Neurobiol. 43, 1–36.
2. Sapolsky, R. M., Krey, L. C. and McEwen, B. S. (1986) The neuroendocrinology of stress and aging: the glucocorticoid cascade hypothesis. Endocrin. Rev. 7, 284–301; Landfield, P. W. (1994) The role of glucocorticoids in brain aging and Alzheimer's disease: an integrative physiological hypothesis. Exp. Gerontol. 29, 3–11; Seckl, J. R. and Olsson, T. (1995) Glucocorticoid hypersecretion and the age-impaired hippocarnpus: cause or effect? J. Endocrinol. 145, 201–211.
3. Morales, A. J., Nolan, J. J., Nelson, J. C. and Yen, S. S. (1994) J. Clin. Endocrinol. Metab. 78, 1360–1367; Bellino, F. L., Daynes, R. Y., Momsby, P. J., Lavrin, D. H. and Nestler, J. E. (1995). Dehydroepiandrosterone and aging. Ann NY Acad Sci 774, 1–351.
4. Meusy-Dessolle, N. and Dang, D. C. (1985). Plasma concentrations of testosterone, dihydrotestosterone, delta 4-androstenedione, dehydroepiandrosterone and estradiol-17beta in the crab-eating monkey (Macaca fascicularis) from birth to adulthood. J. Reprod. Fert. 74, 347–359; Orentreich, N., Brind, J. L., Vogelman, J. H., Andres, R. and Baldwin, H. (1992). Long-term longitudinal measurements of plasma dehydroepiandrosterone sulfate in normal men. J. Clin. Endocrinol. Metab. 75, 1002–1004; Sapolsky, R. M., Vogelman, J. H., Orentreich, N., and Altmann, J. (1993). Senescent decline in serum dehydroepiandrosterone sulfate concentrations in a population of wild baboons. J. Gerontol. 48, B196–200; Belanger, A., Candas, B., Dupont, A., Cusan, L., Diamond, P., Gomez, J. L., and Labrie, F. (1994). Changes in serum concentrations of conjugated and unconjugated steroids in 40- to 80-year-old men. J. Clin. Endocrinol. Metab. 79, 1086–1090; Birkenhager-Gillesse, E. G., Derksen, J., and Lagaay, A. M. (1994). Dehydroepiandrosterone sulphate (DHEAS) in the oldest old, aged 85 and over. Ann. NY Acad. Sci. 719, 543–552; Shealy, C. N. (1995). A review of dehydroepiandrosterone (DHEA). Integ. Physiol. Behav. Sci 30, 308–313.
5. Flood, J. F., Smith, G. E., and Roberts, E. (1988). Dehydroepiandrosterone and its sulfate enhance memory retention in mice. Brain Res. 447, 269–278; Flood, J. F. and Roberts, E. (1988). Dehydroepiandrosterone sulfate improves memory in aging mice. Brain Res. 448, 178–181; Flood, J. F., Morley, J. E., and Roberts, E. (1992). Memory-enhancing effects in male mice of pregnenolone and steroids metabolically derived from it Proc. Natl. Acad. Sci. USA 89, 1567–1571; Flood, J. F., Morley, J. E., and Roberts, E. (1995). Pregnenolone sulfate enhances post-training memory processes when injected in very low doses into limbic system structures: the amygdala is by far the most sensitive. Proc. Natl. Acad. Sci. USA 92, 10806–10810; Yoo, A., Harris, J., and Dubrovsky, B. (1996). Dose-response study of dehydroepiandrosterone sulfate on dentate gyrus long-term potentiation. Exp. Neurol. 137, 151–156; Robel, P. and Baulieu, E. E. (1995). Dehydroepiandrosterone (DHEA) is a neuroactive neurosteroid. Ann. NY Acad. Sci. 774, 82–110; Mayo, W., Dellu, F., Robel, P., Cherkaoui, J., Le Moal, M., and Baulieu, E. E. (1993). Infusion of neurosteroids into the nucleus basilis magnocellularis affects cognitive processes in the rat. Brain Res. 607, 324–328; Mathis, C., Paul, S. M., and. Crawley, J. N. (1994). The neurosteroid pregnenolone sulfate blocks NMDA antagonist-induced deficits in a passive avoidance memory task. Psychopharmacology 116, 201–206; Isaacson, R. L., Vanier, J. A., Baars, J. M., and de Wied, D. (1995). The effects of pregnenolone sulfate and ethylestrenol on retention of a passive avoidance task. Brain Res. 689, 79–84.
6. Stapleton, G., Steel, M., Richardson, M., Mason, J. O., Rose, K. A., Morris, R. G. M., and Lathe, R. (1995). A novel cytochrome P450 expressed primarily in brain. J. Biol. Chem. 270, 29739–29745.
7. Robel, P. & Baulieu, E. E. (1995). In: P. E. Micevych & R. P. Hammer, eds. *Neurobiological Effects of Sex Steroid Hormones* (Cambridge: Cambridge University Press), pp. 281–296.
8. Guarneri, P., Guarneri, R., Cascio, C., Pavasant, P., Piccoli, F. & Papadopoulos, V. (1994) *J. Neurochem.* 63, 86–96
9. Jung-Testas, I., Hu, Z. Y., Baulieu, E. E. & Robel, P. (1996). *J. Steroid Biochem.* 34, 511–519
10. Martini, L. & Melcangi, R. C. (1991). *J. Steroid Biochem. Molec. Biol.* 39, 819–828
11. Walther, B., Ghersi-Egea, J. F., Minn, A. & Siest, G. (1986). *Brain Res.* 375, 338–344
12. Kapitulnik, J., Gelboin, H. V., Guengerich, F. P. & Jacobowitz, D. M. (1987). *Neuroscience* 20, 829–833
13. Warner, M., Kohler, C., Hansson, T. & Gustafsson, J. Å. (1988). *J. Neurochem.* 50, 1057–1065
14. Warner, M., Stromstedt, M., Möller, L. & Gustafsson, J. Å. (1989). *Endocrinology* 124, 2699–2706
15. Warner, M., Wyss, A., Yoshida, S. & Gustafsson, J. Å. (1994). *Meth. Neurosci.* 22, 51–66
16. Warner, M. & Gustafsson, J. Å. (1995). *Front. Neuroendocrinol.* 16, 224–236
17. Akwa, Y., Morfin, R. F. & Baulieu, E. E. (1992). *Biochem. J.* 288, 959–964
18. Bhamre, S., Anandatheerathavarada, H. K., Shankar, S. K. & Ravindranath, V. (1992). *Biochem. Pharmacol.* 44, 1223–1225
19. Bhamre, S., Anandatheerathavarada, H. K., Shankar, S. K., Boyd, M. R. & Ravindranath, V. (1993). *Arch. Biochem. Biophys.* 301, 251–255
20. Komori, M. (1993). *Biochem. Biophys. Res. Comm.* 196, 721–728
21. Stromstedt, M., Warner, M. & Gustafsson, J. Å. (1994). *J. Neurochem.* 63, 671–676
22. Kawashima, H. & Strobel, H. W. (1995). *Biochem. Biophys. Res. Comm.* 209, 535–540
23. Le Goascogne, C., Robel, P., Gouezou, M., Sananes, N., Baulieu, E. E. & Waterman, M. (1987). *Science* 237, 1212–1215
24. Mellon, S. H. & Deschepper, C. F. (1993). *Brain Res.* 629, 283–292
25. Sanne, J. L. & Krueger, K. E. (1995). *J. Neurochem.* 65, 528–536
26. Lauber, M. E. & Lichtensteiger, W. (1994). *Endocrinology* 135, 1661–1668
27. Khanna, M., Qin, K. N., Wang, D. P. & Cheng, K. C. (1995). *J. Biol. Chem.* 270, 20162–20168
28. Guennoun, R., Fiddes, R. J., Gouézou, M., Lombés, M. & Baulieu, E. E. (1995). *Mol. Brain Res.* 30, 287–300
29. Rajan, V., Edwards, C. R. W. & Secki, J. R. (1996). *J. Neurosci.* 16, 65–70
30. Chung, B. C., Picado-Leonard, J., Haniu, M., Bienkowski, M., Hall, P. F., Shively, J. E. & Miller, W. L. (1987). *Proc. Natl. Acad. Sci. USA* 84, 407–411
31. Noshiro, M. & Okuda, K. (1990). *FEBS Lett.* 268, 137–140
32. Noshiro, M., Nishimoto, M., Morohashi, K. & Okuda, K. (1989). *FEBS Lett.* 257, 97–100
33. Jelinek, D. F., Andersson, S., Slaughter, C. A. & Russell, D. W. (1990). *J. Biol. Chem.* 265, 8190–8197

What is claimed is:

1. A method for treating a human or animal requiring therapy for a neuropsychiatric disorder or for inducing cognitive enhancement comprising the administration of an effective amount of a 7α-hydroxy or 7-oxo substituted 3β-hydroxy-steroid having the carbon skeleton of estradiol or derivative thereof independently substituted at one or both of the 7- and 3-positions by an ester or ether group.

2. A method according to claim 1 wherein said neuropsychiatric disorder is selected from (a) Deficits of cognition in aging
(b) Alzheimer's disease and
(c) Depression.

3. A method as claimed in claim 1 wherein the steroid is of formula

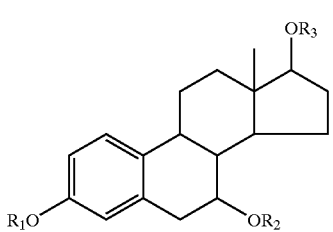

Ia

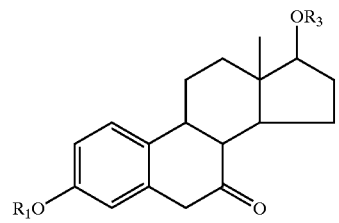

Ib wherein each $R_1$, $R_2$ and $R_3$ are independently selected from the group consisting of hydrogen, substituted or unsubstituted $C_{1-6}$ alkyl groups, groups $R_5CO$—, wherein $R_5$ may be selected from substituted or unsubstituted $C_{1-6}$ alkyl groups, and groups of the formula —$OP(OH)_3$, wherein any substituents are selected from OH, F, Cl, Br, I, amino, $C_{1-6}$ alkylamino, $C_{1-6}$ dialkylamino, COOH or $COOR_4$ wherein $R_4$ represents a $C_{1-6}$ alkyl group; and wherein the compounds may be in free form or in the form of acid addition salts with pharmacologically acceptable anions.

4. A method as claimed in claim 1 wherein the steroid possesses the carbon skeleton of estradiol and has a 3β-substituent-$OR_1$ and/or a 7α-substituent —$OR_2$ where —$OR_1$ and —$OR_2$ each independently represents a free hydroxy, ester or ether group wherein each of $R_1$ and $R_2$ are independently selected from the group consisting of hydrogen, substituted or unsubstituted $C_{1-6}$ alkyl groups, groups $R_5CO$—, wherein $R_5$ may be selected from substituted or unsubstituted $C_{1-6}$ alkyl groups, and groups of the formula —OP(OH)$_3$, wherein any substituents are selected from OH, F, Cl, Br, I, amino, $C_{1-6}$ alkylamino, $C_{1-6}$ dialkylamino, COOH or COOR$_4$ wherein $R_4$ represents a $C_{1-6}$ alkyl group; and wherein the compounds may be in free form or in the form of acid addition salts with pharmacologically acceptable anions.

5. A method as claimed in claim 1 wherein the steroid is 7α-hydroxyestradiol.

* * * * *

SEQUENCE LISTING

<160> NUMBER OF SEQ ID NOS: 6

<210> SEQ ID NO 1
<211> LENGTH: 1763
<212> TYPE: DNA
<213> ORGANISM: Rattus sp.
<220> FEATURE:
<221> NAME/KEY: CDS
<222> LOCATION: (1)..(1242)

<400> SEQUENCE: 1

| | | | | | | | | | | | | | | | | |
|---|---|---|---|---|---|---|---|---|---|---|---|---|---|---|---|---|
| gcc | ttg | gag | tac | cag | tat | gta | atg | aaa | aac | cca | aaa | caa | tta | agc | ttt | 48 |
| Ala | Leu | Glu | Tyr | Gln | Tyr | Val | Met | Lys | Asn | Pro | Lys | Gln | Leu | Ser | Phe | |
| 1 | | | | 5 | | | | | 10 | | | | | 15 | | |
| gag | aag | ttc | agc | cga | aga | tta | tca | gcg | aaa | gcc | ttc | tct | gtc | aag | aag | 96 |
| Glu | Lys | Phe | Ser | Arg | Arg | Leu | Ser | Ala | Lys | Ala | Phe | Ser | Val | Lys | Lys | |
| | | | 20 | | | | | 25 | | | | | 30 | | | |
| ctg | cta | act | aat | gac | gac | ctt | agc | aat | gac | att | cac | aga | ggc | tat | ctt | 144 |
| Leu | Leu | Thr | Asn | Asp | Asp | Leu | Ser | Asn | Asp | Ile | His | Arg | Gly | Tyr | Leu | |
| | | 35 | | | | | 40 | | | | | 45 | | | | |
| ctt | tta | caa | ggc | aaa | tct | ctg | gat | ggt | ctt | ctg | gaa | acc | atg | atc | caa | 192 |
| Leu | Leu | Gln | Gly | Lys | Ser | Leu | Asp | Gly | Leu | Leu | Glu | Thr | Met | Ile | Gln | |
| 50 | | | | | 55 | | | | | 60 | | | | | | |
| gaa | gta | aaa | gaa | ata | ttt | gag | tcc | aga | ctg | cta | aaa | ctc | aca | gat | tgg | 240 |
| Glu | Val | Lys | Glu | Ile | Phe | Glu | Ser | Arg | Leu | Leu | Lys | Leu | Thr | Asp | Trp | |
| 65 | | | | | 70 | | | | | 75 | | | | | 80 | |
| aat | aca | gca | aga | gta | ttt | gat | ttc | tgt | agt | tca | ctg | gta | ttt | gaa | atc | 288 |
| Asn | Thr | Ala | Arg | Val | Phe | Asp | Phe | Cys | Ser | Ser | Leu | Val | Phe | Glu | Ile | |
| | | | | 85 | | | | | 90 | | | | | 95 | | |
| aca | ttt | aca | act | ata | tat | gga | aaa | att | ctt | gct | gct | aac | aaa | aaa | caa | 336 |
| Thr | Phe | Thr | Thr | Ile | Tyr | Gly | Lys | Ile | Leu | Ala | Ala | Asn | Lys | Lys | Gln | |
| | | | 100 | | | | | 105 | | | | | 110 | | | |
| att | atc | agt | gag | ctg | agg | gat | gat | ttt | tta | aaa | ttt | gat | gac | cat | ttc | 384 |
| Ile | Ile | Ser | Glu | Leu | Arg | Asp | Asp | Phe | Leu | Lys | Phe | Asp | Asp | His | Phe | |
| | | 115 | | | | | 120 | | | | | 125 | | | | |
| cca | tac | tta | gta | tct | gac | ata | cct | att | cag | ctt | cta | aga | aat | gca | gaa | 432 |
| Pro | Tyr | Leu | Val | Ser | Asp | Ile | Pro | Ile | Gln | Leu | Leu | Arg | Asn | Ala | Glu | |
| 130 | | | | | 135 | | | | | 140 | | | | | | |
| ttt | atg | cag | aag | aaa | att | ata | aaa | tgt | ctc | aca | cca | gaa | aaa | gta | gct | 480 |
| Phe | Met | Gln | Lys | Lys | Ile | Ile | Lys | Cys | Leu | Thr | Pro | Glu | Lys | Val | Ala | |
| 145 | | | | | 150 | | | | | 155 | | | | | 160 | |
| cag | atg | caa | aga | cgg | tca | gaa | att | gtt | cag | gag | agg | cag | gag | atg | ctg | 528 |
| Gln | Met | Gln | Arg | Arg | Ser | Glu | Ile | Val | Gln | Glu | Arg | Gln | Glu | Met | Leu | |
| | | | | 165 | | | | | 170 | | | | | 175 | | |
| aaa | aaa | tac | tac | ggg | cat | gaa | gag | ttt | gaa | ata | gga | gca | cat | cat | ctt | 576 |
| Lys | Lys | Tyr | Tyr | Gly | His | Glu | Glu | Phe | Glu | Ile | Gly | Ala | His | His | Leu | |
| | | | 180 | | | | | 185 | | | | | 190 | | | |
| ggc | ttg | ctc | tgg | gcc | tct | cta | gca | aac | acc | att | cca | gct | atg | ttc | tgg | 624 |
| Gly | Leu | Leu | Trp | Ala | Ser | Leu | Ala | Asn | Thr | Ile | Pro | Ala | Met | Phe | Trp | |
| | | 195 | | | | | 200 | | | | | 205 | | | | |
| gca | atg | tat | tat | ctt | ctt | cag | cat | cca | gaa | gct | atg | gaa | gtc | ctg | cgt | 672 |
| Ala | Met | Tyr | Tyr | Leu | Leu | Gln | His | Pro | Glu | Ala | Met | Glu | Val | Leu | Arg | |
| | | | 210 | | | | | 215 | | | | | 220 | | | |
| gac | gaa | att | gac | agc | ttc | ctg | cag | tca | aca | ggt | caa | aag | aaa | gga | cct | 720 |
| Asp | Glu | Ile | Asp | Ser | Phe | Leu | Gln | Ser | Thr | Gly | Gln | Lys | Lys | Gly | Pro | |
| 225 | | | | | 230 | | | | | 235 | | | | | 240 | |
| gga | att | tct | gtc | cac | ttc | acc | aga | gaa | caa | ttg | gac | agc | ttg | gtc | tgc | 768 |
| Gly | Ile | Ser | Val | His | Phe | Thr | Arg | Glu | Gln | Leu | Asp | Ser | Leu | Val | Cys | |
| | | | | 245 | | | | | 250 | | | | | 255 | | |

```
ctg gaa agc gct att ctt gag gtt ctg agg ttg tgc tcc tac tcc agc      816
Leu Glu Ser Ala Ile Leu Glu Val Leu Arg Leu Cys Ser Tyr Ser Ser
        260                 265                 270 atc atc cgt gaa gtg caa gag gat atg gat ttc agc tca gag agt agg      864
Ile Ile Arg Glu Val Gln Glu Asp Met Asp Phe Ser Ser Glu Ser Arg
            275                 280                 285 agc tac cgt ctg cgg aaa gga gac ttt gta gct gtc ttt cct cca atg      912
Ser Tyr Arg Leu Arg Lys Gly Asp Phe Val Ala Val Phe Pro Pro Met
        290                 295                 300 ata cac aat gac cca gaa gtc ttc gat gct cca aag gac ttt agg ttt      960
Ile His Asn Asp Pro Glu Val Phe Asp Ala Pro Lys Asp Phe Arg Phe
305                 310                 315                 320 gat cgc ttc gta gaa gat ggt aag aag aaa aca acg ttt ttc aaa gga     1008
Asp Arg Phe Val Glu Asp Gly Lys Lys Lys Thr Thr Phe Phe Lys Gly
                325                 330                 335 gga aaa aag ctg aag agt tac att ata cca ttt gga ctt gga aca agc     1056
Gly Lys Lys Leu Lys Ser Tyr Ile Ile Pro Phe Gly Leu Gly Thr Ser
            340                 345                 350 aaa tgt cca ggc aga tac ttt gca att aat gaa atg aag cta cta gtg     1104
Lys Cys Pro Gly Arg Tyr Phe Ala Ile Asn Glu Met Lys Leu Leu Val
        355                 360                 365 att ata ctt tta act tat ttt gat tta gaa gtc att gac act aag cct     1152
Ile Ile Leu Leu Thr Tyr Phe Asp Leu Glu Val Ile Asp Thr Lys Pro
370                 375                 380 ata gga cta aac cac agt cgc atg ttt ctg ggc att cag cat cca gac     1200
Ile Gly Leu Asn His Ser Arg Met Phe Leu Gly Ile Gln His Pro Asp
385                 390                 395                 400 tct gac atc tca ttt agg tac aag gca aaa tct tgg aga tcc              1242
Ser Asp Ile Ser Phe Arg Tyr Lys Ala Lys Ser Trp Arg Ser
                405                 410 tgaaagggtg gcagagaagc ttagcggaat aaggctgcac atgctgagct ctgtgatttg    1302
ctgtactccc caaatgcagc cactattctt gtttgttaga aaatggcaaa tttttatttg    1362
attgcgatcc atccagtttg ttttgggtca caaaacctgt cataaaataa agcgctgtca    1422
tggtgtaaaa aaatgtcatg gcaatcattt caggataagg taaataacg ttttcaagtt     1482 tgtacttact atgattttta tcatttgtag tgaatgtgct tttccagtaa taaatttgcg    1542
ccagggtgat ttttttttaat tactgaaatc ctctaatatc ggttttatgt gctgccagaa   1602
aagtgtgcca tcaatggaca gtataacaat ttccagtttt ccagagaagg gagaaattaa    1662
gccccatgag ttacgctgta taaaattgtt ctcttcaact ataatatcaa taatgtctat    1722
atcaccaggt tacctttgca ttaaatcgag ttttgcaaaa g                        1763

<210> SEQ ID NO 2
<211> LENGTH: 1880
<212> TYPE: DNA
<213> ORGANISM: Murine sp.
<220> FEATURE:
<221> NAME/KEY: CDS
<222> LOCATION: (81)..(1601)

<400> SEQUENCE: 2
ggcaggcaca gcctctggtc taagaagaga gggcactgtg cagaagccat cgctccctac     60
agagccgcca gctcgtcggg atg cag gga gcc acg acc cta gat gcc gcc tcg    113
                        Met Gln Gly Ala Thr Thr Leu Asp Ala Ala Ser
                         1               5                  10 cca ggg cct ctc gcc ctc cta ggc ctt ctc ttt gcc gcc acc tta ctg      161
Pro Gly Pro Leu Ala Leu Leu Gly Leu Leu Phe Ala Ala Thr Leu Leu
            15                  20                  25
```

-continued

| | | |
|---|---|---|
| ctc tcg gcc ctg ttc ctc ctc acc cgg cgc acc agg cgc cct cgt gaa<br>Leu Ser Ala Leu Phe Leu Leu Thr Arg Arg Thr Arg Arg Pro Arg Glu<br>30                        35                  40 | 209 |
| cca ccc ttg ata aaa ggt tgg ctt cct tat ctt ggc atg gcc ctg aaa<br>Pro Pro Leu Ile Lys Gly Trp Leu Pro Tyr Leu Gly Met Ala Leu Lys<br>       45                    50                  55 | 257 |
| ttc ttt aag gat ccg tta act ttc ttg aaa act ctt caa agg caa cat<br>Phe Phe Lys Asp Pro Leu Thr Phe Leu Lys Thr Leu Gln Arg Gln His<br>60                        65                    70              75 | 305 |
| ggt gac act ttc act gtc ttc ctt gtg ggg aag tat ata aca ttt gtt<br>Gly Asp Thr Phe Thr Val Phe Leu Val Gly Lys Tyr Ile Thr Phe Val<br>               80                    85                  90 | 353 |
| ctg aac cct ttc cag tac cag tat gta acg aaa aac cca aaa caa tta<br>Leu Asn Pro Phe Gln Tyr Gln Tyr Val Thr Lys Asn Pro Lys Gln Leu<br>95                        100                 105 | 401 |
| agc ttt cag aag ttc agc agc cga tta tca gcg aaa gcc ttc tct gta<br>Ser Phe Gln Lys Phe Ser Ser Arg Leu Ser Ala Lys Ala Phe Ser Val<br>          110                 115                120 | 449 |
| aag aag ctg ctt act gat gac gac ctt aat gaa gac gtt cac aga gcc<br>Lys Lys Leu Leu Thr Asp Asp Asp Leu Asn Glu Asp Val His Arg Ala<br>125                      130                 135 | 497 |
| tat cta ctt cta caa ggc aaa cct ttg gat gct ctt ctg gaa act atg<br>Tyr Leu Leu Leu Gln Gly Lys Pro Leu Asp Ala Leu Leu Glu Thr Met<br>140                      145                150                155 | 545 |
| atc caa gaa gta aaa gaa tta ttt gag tcc caa ctg cta aaa atc aca<br>Ile Gln Glu Val Lys Glu Leu Phe Glu Ser Gln Leu Leu Lys Ile Thr<br>                 160                    165                170 | 593 |
| gat tgg aac aca gaa aga ata ttt gca ttc tgt ggc tca ctg gta ttt<br>Asp Trp Asn Thr Glu Arg Ile Phe Ala Phe Cys Gly Ser Leu Val Phe<br>                    175                    180                185 | 641 |
| gag atc aca ttt gcg act cta tat gga aaa att ctt gct ggt aac aag<br>Glu Ile Thr Phe Ala Thr Leu Tyr Gly Lys Ile Leu Ala Gly Asn Lys<br>          190                 195                200 | 689 |
| aaa caa att atc agt gag cta agg gat gat ttt ttt aaa ttt gat gac<br>Lys Gln Ile Ile Ser Glu Leu Arg Asp Asp Phe Phe Lys Phe Asp Asp<br>205                      210                 215 | 737 |
| atg ttc cca tac tta gta tct gac ata cct att cag ctt cta aga aat<br>Met Phe Pro Tyr Leu Val Ser Asp Ile Pro Ile Gln Leu Leu Arg Asn<br>220                      225                230                235 | 785 |
| gaa gaa tct atg cag aag aaa att ata aaa tgc ctc aca tca gaa aaa<br>Glu Glu Ser Met Gln Lys Lys Ile Ile Lys Cys Leu Thr Ser Glu Lys<br>                    240                    245                250 | 833 |
| gta gct cag atg caa gga cag tca aaa att gtt cag gaa agc caa gat<br>Val Ala Gln Met Gln Gly Gln Ser Lys Ile Val Gln Glu Ser Gln Asp<br>          255                 260                265 | 881 |
| ctg ctg aaa aga tac tat agg cat gac gat tct gaa ata gga gca cat<br>Leu Leu Lys Arg Tyr Tyr Arg His Asp Asp Ser Glu Ile Gly Ala His<br>270                      275                 280 | 929 |
| cat ctt ggc ttt ctc tgg gcc tct cta gca aac acc att cca gct atg<br>His Leu Gly Phe Leu Trp Ala Ser Leu Ala Asn Thr Ile Pro Ala Met<br>285                      290                295 | 977 |
| ttc tgg gca atg tat tat att ctt cgg cat cct gaa gct atg gaa gcc<br>Phe Trp Ala Met Tyr Tyr Ile Leu Arg His Pro Glu Ala Met Glu Ala<br>300                      305                310                315 | 1025 |
| ctg cgt gac gaa att gac agt ttc ctg cag tca aca ggt caa aag aaa<br>Leu Arg Asp Glu Ile Asp Ser Phe Leu Gln Ser Thr Gly Gln Lys Lys<br>                    320                    325                330 | 1073 |
| ggg cct gga att tca gtc cac ttc acc aga gaa caa ttg gac agc ttg<br>Gly Pro Gly Ile Ser Val His Phe Thr Arg Glu Gln Leu Asp Ser Leu<br>          335                 340                345 | 1121 |

| | | |
|---|---|---|
| gtc tgc ctg gaa agc act att ctt gag gtt ctg agg ctg tgc tca tac<br>Val Cys Leu Glu Ser Thr Ile Leu Glu Val Leu Arg Leu Cys Ser Tyr<br>                350                    355                    360 | | 1169 |
| tcc agc atc atc cga gaa gtg cag gag gat atg aat ctc agc tta gag<br>Ser Ser Ile Ile Arg Glu Val Gln Glu Asp Met Asn Leu Ser Leu Glu<br>365                    370                    375 | | 1217 |
| agt aag agt ttc tct ctg cgg aaa gga gat ttt gta gcc ctc ttt cct<br>Ser Lys Ser Phe Ser Leu Arg Lys Gly Asp Phe Val Ala Leu Phe Pro<br>380                    385                    390                    395 | | 1265 |
| cca ctc ata cac aat gac ccg gaa atc ttc gat gct cca aag gaa ttt<br>Pro Leu Ile His Asn Asp Pro Glu Ile Phe Asp Ala Pro Lys Glu Phe<br>                400                    405                    410 | | 1313 |
| agg ttc gat cgg ttc ata gaa gat ggt aag aag aaa agc acg ttt ttc<br>Arg Phe Asp Arg Phe Ile Glu Asp Gly Lys Lys Lys Ser Thr Phe Phe<br>                415                    420                    425 | | 1361 |
| aaa gga ggg aag agg ctg aag act tac gtt atg cct ttt gga ctc gga<br>Lys Gly Gly Lys Arg Leu Lys Thr Tyr Val Met Pro Phe Gly Leu Gly<br>            430                    435                    440 | | 1409 |
| aca agc aaa tgt cca ggg aga tat ttt gca gtg aac gaa atg aag cta<br>Thr Ser Lys Cys Pro Gly Arg Tyr Phe Ala Val Asn Glu Met Lys Leu<br>            445                    450                    455 | | 1457 |
| ctg ctg att gag ctt tta act tat ttt gat tta gaa att atc gac agg<br>Leu Leu Ile Glu Leu Leu Thr Tyr Phe Asp Leu Glu Ile Ile Asp Arg<br>460                    465                    470                    475 | | 1505 |
| aag cct ata ggg cta aat cac agt cgg atg ttt tta ggt att cag cac<br>Lys Pro Ile Gly Leu Asn His Ser Arg Met Phe Leu Gly Ile Gln His<br>                480                    485                    490 | | 1553 |
| ccc gat tct gcc gtc tcc ttt agg tac aaa gca aaa tct tgg aga agc<br>Pro Asp Ser Ala Val Ser Phe Arg Tyr Lys Ala Lys Ser Trp Arg Ser<br>            495                    500                    505 | | 1601 |
| tgaaagtgtg gcagagaagc tttgcagagt aaggctgcat gtgctgagct ccgtgatttg | | 1661 |
| gtgcactccc ccaaatgcaa ccgctactct tgtttgaaaa tggcaaattt atatttggtt | | 1721 |
| gagatcaatc cagttggttt tgggtcacaa aacctgtcat aaaataaagc agtgtgatgg | | 1781 |
| tttaaaaaat gtcatggcaa tcatttcagg ataaggtaaa ataacatttt caagtttgta | | 1841 |
| cttactatga tttttatcat ttgtagtgaa tgtgcttttt | | 1880 |

<210> SEQ ID NO 3
<211> LENGTH: 3846
<212> TYPE: DNA
<213> ORGANISM: Homo sapiens
<220> FEATURE:
<223> OTHER INFORMATION: "n" at various positions throughout the
     sequence may be a, t, c, g, other or unknown

<400> SEQUENCE: 3

| | |
|---|---|
| ggatccaacc aagtttccag atcttataaa tgtggtgaat ggtgaatgac ttcctgaaga | 60 |
| atggatgaat ggatgtgttc tagtttggaa tcctgtgtca gtcacaagtc aatatgtgac | 120 |
| cttgaacatg ttattaaatc tcccacatcc ataaagtgaa aatgctggc attagtggat | 180 |
| ttttgccagt gttgaattag acatttattt gtgagtacct gctccataca gtatggtcat | 240 |
| ttatttgagt taaaattgtt gtatttgaac aaaaactcaga tgacacctaa gcatgaaaaa | 300 |
| gctctttatg aagtataaat actcagaaat ggaatgcat gttgccaatt tgttttctgc | 360 |
| tttattgagg gaaatatatg agaagtattt aagtcagggg attatgagga atatttaaag | 420 |
| gatannnnnn nnnnnnnnnn nnnnnnnnnn nnnnnnnnnn nnnnnnnnnn nnnnnnnnnn | 480 |
| nnnnnnnnnn nnnnnnnnnn nnnnnnnnnn nnnnnnnnnn nnnnnnnnnn nnnnnnnnnn | 540 |

-continued

```
nnnnnnnnnn nnnnnnnnnn nnnnnnnnnn nnnnnnnnnn nnnnnnnnnn nnnnnnnnnn        600
nnnnnnnnnn nnnnnnnnnn nnnnnnnnnn nnnntctaga gtgttttcca ccatctttca        660
aaggaaacat gtagtgtacc ttcgaatgaa atggatttgt attaaacttt ttgccttagt        720
tattagggtc tttctaattt ttgattaaca tatttttta atttgtggtg tttatttctg        780
tttttattaa caaacgaact catatgctcc tctctctttt ttttttttct ggaaagtaca        840
taacatttat acctggaccc ttccagtacc agctagtgat aaaaaatcat aaacaattaa        900
gctttcgagt atcttctaat aaattatcag agaaagcatt tagcatcagt cagttgcaaa        960
aaaatcatga catgaatgat gagcttcacc tctgctatca attttttgcaa ggcaaatctt      1020
tggacatact cttggaaagc atgatgcaga atctaaaaca agttttttgaa ccccagctgt      1080
taaaaaccac aagttgggac acggcagaac tgtatccatt ctgcagctca ataatatttg      1140
agatcacatt tacaactata tatggaaaag ttattgtttg tgacaacaac aaatttatta      1200
gtgagctaag agatgatttt ttaaaatttg atgacaagtt tgcatattta gtatccaaca      1260
tacccattga gcttctagga aatgtcaagt ctattagaga gaaaattata aaatgcttct      1320
catcagaaaa gttagccaag atgcaaggat ggtcagaagt ttttcaaagc aggcaagatg      1380
acctggagaa atattatgtg cacgaggacc ttgaaatagg aggtaagaac ttctgaatga      1440
gcacttgcct aaataaaaat catttacata gacctctgaa ataaaaaaag acaaaatggc      1500
gaccttgaaa atttttttat gctctttcta attggctaat gataaatgtt tactctgata      1560
taacctctat aattgatatt ttttttttg ctgaggtggt aaacagatac ttaatggtga       1620
taatgagaaa gcgtataact aagctgcatt tatccctctt atctcatccc cgaccacacc      1680
gccccccca tacacattac attttaaact attctcatta agcagaaaat tagacttcag      1740
aagcctattg gttctcatta gcatgcagtg atccttggct ggtctgtgtc ctaacatctt      1800
ttaattagca cactgcaaat ctaatcagtg taataaacgc tattaatctt cctttacact      1860
tattttctcc cacacatcat ttaggctttc tctgggcctc tgtggcaaac actattccaa      1920
ctatgttctg ggcaacgtat tatccttctgc ggcacccaga agctatggca gcagtgcgtg      1980
acgaaattga ccgtttgctg cagtcaacag gtcaaaagga agggtctgga tttcccatcc      2040
acctcaccag agaacaattg gacagcctaa tctgcctagg taattatttt atctgttatg      2100
aagaaagaag gtacctctct gcaaactcgg tttatcactc atagctgttt acaagaggta      2160
gaggacacag ctgctaattg acataataac tcccatttac atcaattata aattatgtag      2220
tttatagccg tagatcatct cattgcatgt aaacataagg cctatgtaat taactgtgta      2280
atgtatgtaa aattctaacc aaagcttnnn nnnnnnnnn nnnnnnnnnn nnnnnnnnnn       2340
nnnnnnnnnn nnnnnnnnnn nnnnnnnnnn nnnnnnnnnn nnnnnnnnnn nnnnnnnnnn      2400
nnnnnnnnnn nnnnnnnnnn nnnnnnnnnn nnnnnnnnnn nnnnnnnnnn nnnnnnnnnn      2460
nnnnnnnnnn nnnnnnnnnn nnnnnnnnnn nnnnnnnnnn nnnnnnnnnn nnnnnnnnnn      2520
nnnnnnnnnn nnnnnnnnnn nnnnnnnnnn nnnnnnnnnn nnnnnnnnnn nnnnnnnnnn      2580
nnnnnnnnnn nnnnnnnnnn nnnnnnnnnn nnnnnnnnnn nnnnnnnnnn nnnnnnnnnn      2640
nnnnnnnnnn nnnnnnnnnn nnnnnnnnnn nnnnnnnnnn nnnnnnnnnn nnnnnnnnnn      2700
nnnnnnnnnn nnnnnnnnnn nnnnnnnnnn nnnnnnnnnn nnnnnnnnnn nnnnnnnnnn      2760
nnnnnnnnnn nnnnnnnnnn nnnnnnnnnn nnnnnnnnnn nnnnnnnnnn nnnnnnnnnn      2820
nnnnnnnnnn nnnnnnnnnn nnnnnnnnnn nnnnnncct gactgaactt cttactgcca       2880
aagttaaatt ccataccaat gagttattct ctattctctc tgtattgaca tttcatctgc      2940
```

```
ggtatccttt agggtacaat gagttattct ctattctctc tgtattgaca tttcatctgc    3000
ggtatccttt agggtacaat attccaagtt tctttagaca aacgcaggaa caaatgttca    3060
catatttctg tttctttatt cctttgacaa gtaggcgagc attttagcct atgttggtct    3120
caaaaaaaat cttttaaata tgttccaggt tctttaatgg gacctttcag gagcaaaagt    3180
cctcccaggt ttggtcaatg ttcaccctcn gtggccattg aggaaaatgc ccnnnnngtt    3240
ctagagattg ttctcacttc tcaggctaag gcccattgag caatgccaga agcatgcct    3300 tatactagca gtcaatttgg aagtttgtag tttgtgtctt tagcataggt tatcaaataa    3360
attttatatt tncttttaaa aaaatctcaa cattactaaa atacaaatat cctttattt    3420 ttctttgcag aattatcggg gaacaaatcc agaaaatttg tgtaaatttc gggtagttgc    3480
tccacttgat acacagtatt tctgcatatt gtaatttcta tgaagatcta ggttgcattt    3540
cccatacatt caagcagttt ccattgcatt tttatgaata agatgacgca tactgggaag    3600
taaggcaaat acactaaaag gaatatgtgt ttgtattctg tatagttatt actcttaaaa    3660
aaagtagttg taattcatcc actcttttta ctttcaactt tttgctatta aaaatcatt    3720 tttaaatttc agtattaaag cagaaacatt taaatttatt agaccagaaa aataacagat    3780
tctagaacta aatttgaat ccatttaagc ccatagctag agctagagat tttcactatt    3840
ggatcc                                                              3846

<210> SEQ ID NO 4
<211> LENGTH: 414
<212> TYPE: PRT
<213> ORGANISM: Rattus sp.

<400> SEQUENCE: 4

Ala Leu Glu Tyr Gln Tyr Val Met Lys Asn Pro Lys Gln Leu Ser Phe
  1               5                  10                  15

Glu Lys Phe Ser Arg Arg Leu Ser Ala Lys Ala Phe Ser Val Lys Lys
             20                  25                  30

Leu Leu Thr Asn Asp Asp Leu Ser Asn Asp Ile His Arg Gly Tyr Leu
         35                  40                  45

Leu Leu Gln Gly Lys Ser Leu Asp Gly Leu Leu Glu Thr Met Ile Gln
     50                  55                  60

Glu Val Lys Glu Ile Phe Glu Ser Arg Leu Leu Lys Leu Thr Asp Trp
 65                  70                  75                  80

Asn Thr Ala Arg Val Phe Asp Phe Cys Ser Ser Leu Val Phe Glu Ile
                 85                  90                  95

Thr Phe Thr Thr Ile Tyr Gly Lys Ile Leu Ala Ala Asn Lys Lys Gln
            100                 105                 110

Ile Ile Ser Glu Leu Arg Asp Asp Phe Leu Lys Phe Asp Asp His Phe
        115                 120                 125

Pro Tyr Leu Val Ser Asp Ile Pro Ile Gln Leu Leu Arg Asn Ala Glu
    130                 135                 140

Phe Met Gln Lys Lys Ile Ile Lys Cys Leu Thr Pro Glu Lys Val Ala
145                 150                 155                 160

Gln Met Gln Arg Arg Ser Glu Ile Val Gln Glu Arg Gln Glu Met Leu
                165                 170                 175

Lys Lys Tyr Tyr Gly His Glu Glu Phe Glu Ile Gly Ala His His Leu
            180                 185                 190

Gly Leu Leu Trp Ala Ser Leu Ala Asn Thr Ile Pro Ala Met Phe Trp
        195                 200                 205
```

```
Ala Met Tyr Tyr Leu Leu Gln His Pro Glu Ala Met Glu Val Leu Arg
    210                 215                 220
Asp Glu Ile Asp Ser Phe Leu Gln Ser Thr Gly Gln Lys Lys Gly Pro
225                 230                 235                 240
Gly Ile Ser Val His Phe Thr Arg Glu Gln Leu Asp Ser Leu Val Cys
                245                 250                 255
Leu Glu Ser Ala Ile Leu Glu Val Leu Arg Leu Cys Ser Tyr Ser Ser
                260                 265                 270
Ile Ile Arg Glu Val Gln Glu Asp Met Asp Phe Ser Ser Glu Ser Arg
    275                 280                 285
Ser Tyr Arg Leu Arg Lys Gly Asp Phe Val Ala Val Phe Pro Pro Met
    290                 295                 300
Ile His Asn Asp Pro Glu Val Phe Asp Ala Pro Lys Asp Phe Arg Phe
305                 310                 315                 320
Asp Arg Phe Val Glu Asp Gly Lys Lys Thr Thr Phe Phe Lys Gly
                325                 330                 335
Gly Lys Lys Leu Lys Ser Tyr Ile Ile Pro Phe Gly Leu Gly Thr Ser
                340                 345                 350
Lys Cys Pro Gly Arg Tyr Phe Ala Ile Asn Glu Met Lys Leu Leu Val
        355                 360                 365
Ile Ile Leu Leu Thr Tyr Phe Asp Leu Glu Val Ile Asp Thr Lys Pro
    370                 375                 380
Ile Gly Leu Asn His Ser Arg Met Phe Leu Gly Ile Gln His Pro Asp
385                 390                 395                 400
Ser Asp Ile Ser Phe Arg Tyr Lys Ala Lys Ser Trp Arg Ser
                405                 410

<210> SEQ ID NO 5
<211> LENGTH: 507
<212> TYPE: PRT
<213> ORGANISM: Murine sp.

<400> SEQUENCE: 5

Met Gln Gly Ala Thr Thr Leu Asp Ala Ala Ser Pro Gly Pro Leu Ala
 1               5                  10                  15
Leu Leu Gly Leu Leu Phe Ala Ala Thr Leu Leu Ser Ala Leu Phe
                20                  25                  30
Leu Leu Thr Arg Arg Thr Arg Arg Pro Arg Glu Pro Pro Leu Ile Lys
                35                  40                  45
Gly Trp Leu Pro Tyr Leu Gly Met Ala Leu Lys Phe Phe Lys Asp Pro
        50                  55                  60
Leu Thr Phe Leu Lys Thr Leu Gln Arg Gln His Gly Asp Thr Phe Thr
 65                  70                  75                  80
Val Phe Leu Val Gly Lys Tyr Ile Thr Phe Val Leu Asn Pro Phe Gln
                85                  90                  95
Tyr Gln Tyr Val Thr Lys Asn Pro Lys Gln Leu Ser Phe Gln Lys Phe
                100                 105                 110
Ser Ser Arg Leu Ser Ala Lys Ala Phe Ser Val Lys Lys Leu Leu Thr
        115                 120                 125
Asp Asp Asp Leu Asn Glu Asp Val His Arg Ala Tyr Leu Leu Leu Gln
130                 135                 140
Gly Lys Pro Leu Asp Ala Leu Leu Glu Thr Met Ile Gln Glu Val Lys
145                 150                 155                 160
Glu Leu Phe Glu Ser Gln Leu Leu Lys Ile Thr Asp Trp Asn Thr Glu
                165                 170                 175
```

```
Arg Ile Phe Ala Phe Cys Gly Ser Leu Val Phe Glu Ile Thr Phe Ala
            180                 185                 190

Thr Leu Tyr Gly Lys Ile Leu Ala Gly Asn Lys Lys Gln Ile Ile Ser
            195                 200                 205

Glu Leu Arg Asp Asp Phe Phe Lys Phe Asp Met Phe Pro Tyr Leu
            210                 215                 220

Val Ser Asp Ile Pro Ile Gln Leu Leu Arg Asn Glu Glu Ser Met Gln
225                 230                 235                 240

Lys Lys Ile Ile Lys Cys Leu Thr Ser Glu Lys Val Ala Gln Met Gln
                245                 250                 255

Gly Gln Ser Lys Ile Val Gln Glu Ser Gln Asp Leu Leu Lys Arg Tyr
                260                 265                 270

Tyr Arg His Asp Asp Ser Glu Ile Gly Ala His His Leu Gly Phe Leu
            275                 280                 285

Trp Ala Ser Leu Ala Asn Thr Ile Pro Ala Met Phe Trp Ala Met Tyr
            290                 295                 300

Tyr Ile Leu Arg His Pro Glu Ala Met Glu Ala Leu Arg Asp Glu Ile
305                 310                 315                 320

Asp Ser Phe Leu Gln Ser Thr Gly Gln Lys Lys Gly Pro Gly Ile Ser
                325                 330                 335

Val His Phe Thr Arg Glu Gln Leu Asp Ser Leu Val Cys Leu Glu Ser
            340                 345                 350

Thr Ile Leu Glu Val Leu Arg Leu Cys Ser Tyr Ser Ser Ile Ile Arg
            355                 360                 365

Glu Val Gln Glu Asp Met Asn Leu Ser Leu Glu Ser Lys Ser Phe Ser
            370                 375                 380

Leu Arg Lys Gly Asp Phe Val Ala Leu Phe Pro Pro Leu Ile His Asn
385                 390                 395                 400

Asp Pro Glu Ile Phe Asp Ala Pro Lys Glu Phe Arg Phe Asp Arg Phe
                405                 410                 415

Ile Glu Asp Gly Lys Lys Lys Ser Thr Phe Phe Lys Gly Gly Lys Arg
            420                 425                 430

Leu Lys Thr Tyr Val Met Pro Phe Gly Leu Gly Thr Ser Lys Cys Pro
            435                 440                 445

Gly Arg Tyr Phe Ala Val Asn Glu Met Lys Leu Leu Ile Glu Leu
            450                 455                 460

Leu Thr Tyr Phe Asp Leu Glu Ile Ile Asp Arg Lys Pro Ile Gly Leu
465                 470                 475                 480

Asn His Ser Arg Met Phe Leu Gly Ile Gln His Pro Asp Ser Ala Val
                485                 490                 495

Ser Phe Arg Tyr Lys Ala Lys Ser Trp Arg Ser
                500                 505

<210> SEQ ID NO 6
<211> LENGTH: 266
<212> TYPE: PRT
<213> ORGANISM: Homo sapiens

<400> SEQUENCE: 6

Gly Lys Tyr Ile Thr Phe Ile Pro Gly Pro Phe Gln Tyr Gln Leu Val
1               5                   10                  15

Ile Lys Asn His Lys Asn Leu Ser Phe Arg Val Ser Ser Asn Lys Leu
                20                  25                  30

Ser Glu Lys Ala Phe Ser Ile Ser Gln Leu Gln Lys Asn His Asp Met
            35                  40                  45
```

-continued

```
Asn Asp Glu Leu His Leu Cys Tyr Gln Phe Leu Gln Gly Lys Ser Leu
         50                  55                  60

Asp Ile Leu Leu Glu Ser Met Met Gln Asn Leu Lys Gln Val Phe Glu
 65                  70                  75                  80

Pro Gln Leu Leu Lys Thr Thr Ser Trp Asp Thr Ala Glu Leu Tyr Pro
                 85                  90                  95

Phe Cys Ser Ser Ile Ile Phe Glu Ile Thr Phe Thr Thr Ile Tyr Gly
                100                 105                 110

Lys Val Ile Val Cys Asp Asn Asn Lys Phe Ile Ser Glu Leu Arg Asp
                115                 120                 125

Asp Phe Leu Lys Phe Asp Asp Lys Phe Ala Tyr Leu Val Ser Asn Ile
        130                 135                 140

Pro Ile Glu Leu Leu Gly Asn Val Lys Ser Ile Arg Glu Lys Ile Ile
145                 150                 155                 160

Lys Cys Phe Ser Ser Glu Lys Leu Ala Lys Met Gln Gly Trp Ser Glu
                165                 170                 175

Val Phe Gln Ser Arg Gln Asp Asp Leu Glu Lys Tyr Tyr Val His Glu
                180                 185                 190

Asp Leu Glu Ile Gly Ala His His Phe Gly Phe Leu Trp Val Ser Val
        195                 200                 205

Ala Ser Thr Ile Pro Thr Met Phe Trp Ala Thr Tyr Tyr Leu Leu Arg
        210                 215                 220

His Pro Glu Ala Met Ala Ala Val Arg Asp Glu Ile Asp Arg Leu Leu
225                 230                 235                 240

Gln Ser Thr Gly Gln Lys Glu Gly Ser Gly Phe Pro Ile His Leu Thr
                245                 250                 255

Arg Glu Gln Leu Asp Ser Leu Ile Cys Leu
                260                 265
```